United States Patent
Baheti et al.

(10) Patent No.: US 12,082,943 B2
(45) Date of Patent: *Sep. 10, 2024

(54) SYSTEM AND METHOD FOR VITAL SIGNAL SENSING USING A MILLIMETER-WAVE RADAR SENSOR

(71) Applicant: Infineon Technologies AG, Neubiberg (DE)

(72) Inventors: Ashutosh Baheti, Munich (DE); Reinhard-Wolfgang Jungmaier, Alkoven (AT); Avik Santra, Munich (DE); Saverio Trotta, Munich (DE)

(73) Assignee: Infineon Technologies AG, Neubiberg (DE)

( * ) Notice: Subject to any disclaimer, the term of this patent is extended or adjusted under 35 U.S.C. 154(b) by 142 days.

This patent is subject to a terminal disclaimer.

(21) Appl. No.: 17/652,608

(22) Filed: Feb. 25, 2022

(65) Prior Publication Data
US 2022/0175314 A1   Jun. 9, 2022

Related U.S. Application Data

(62) Division of application No. 15/872,701, filed on Jan. 16, 2018, now Pat. No. 11,278,241.

(51) Int. Cl.
*A61B 5/05*   (2021.01)
*A61B 5/00*   (2006.01)
(Continued)

(52) U.S. Cl.
CPC .............. *A61B 5/681* (2013.01); *A61B 5/024* (2013.01); *A61B 5/02438* (2013.01);
(Continued)

(58) Field of Classification Search
None
See application file for complete search history.

(56) References Cited

U.S. PATENT DOCUMENTS 4,241,347 A   12/1980   Albanese et al.
6,147,572 A   11/2000   Kaminski et al.
(Continued)

FOREIGN PATENT DOCUMENTS

CN   1463161 A   12/2003
CN   1716695 A   1/2006
(Continued)

OTHER PUBLICATIONS

"BT24MTR11 Using BGT24MTR11 in Low Power Applications 24 GHZ Rader," Application Note AN341, Revision: Rev 1.0, Infineon Technologies AG, Munich, Germany, Dec. 2, 2013, 25 pages.
(Continued)

*Primary Examiner* — Meredith Weare
(74) *Attorney, Agent, or Firm* — Slater Matsil, LLP

(57) ABSTRACT

A system includes a millimeter-wave radar sensor disposed on a circuit board, a plurality of antennas coupled to the millimeter-wave radar sensor and disposed on the circuit board, and a processing circuit coupled to the millimeter-wave radar sensor and disposed on the circuit board. The processing circuit is configured to determine vital signal information based on output from the millimeter-wave radar sensor.

20 Claims, 15 Drawing Sheets

(51) Int. Cl.

| | | |
|---|---|---|
| *A61B 5/024* | (2006.01) | |
| *A61B 5/0245* | (2006.01) | |
| *A61B 5/0507* | (2021.01) | |
| *A61B 5/35* | (2021.01) | |
| *G01S 7/03* | (2006.01) | |
| *G01S 7/41* | (2006.01) | |
| *G01S 13/32* | (2006.01) | |
| *G01S 13/536* | (2006.01) | |
| *G01S 13/88* | (2006.01) | |
| *H01L 23/52* | (2006.01) | |
| *H01L 23/538* | (2006.01) | |
| *H01L 25/065* | (2023.01) | |

(52) U.S. Cl.
CPC ...... *A61B 5/02444* (2013.01); *A61B 5/02455* (2013.01); *A61B 5/0507* (2013.01); *A61B 5/35* (2021.01); *A61B 5/6831* (2013.01); *G01S 7/032* (2013.01); *G01S 7/415* (2013.01); *G01S 13/32* (2013.01); *G01S 13/536* (2013.01); *G01S 13/88* (2013.01); *H01L 23/52* (2013.01); *H01L 23/5384* (2013.01); *H01L 23/5385* (2013.01); *H01L 25/0657* (2013.01)

(56) References Cited

U.S. PATENT DOCUMENTS

| | | |
|---|---|---|
| 6,414,631 B1 | 7/2002 | Fujimoto |
| 6,636,174 B2 | 10/2003 | Arikan et al. |
| 7,048,973 B2 | 5/2006 | Sakamoto et al. |
| 7,057,564 B2 | 6/2006 | Tsai et al. |
| 7,171,052 B2 | 1/2007 | Park |
| 7,317,417 B2 | 1/2008 | Arikan et al. |
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,305,255 B2 | 11/2012 | Margomenos |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,413,079 B2 | 8/2016 | Kamgaing et al. |
| 9,495,600 B2 | 11/2016 | Heu et al. |
| 9,886,095 B2 | 2/2018 | Pothier |
| 9,935,065 B1 | 4/2018 | Baheti et al. |
| 11,278,241 B2 * | 3/2022 | Baheti .................... G01S 13/88 |
| 11,346,936 B2 * | 5/2022 | Baheti .................. A61B 5/0022 |
| 2003/0179127 A1 | 9/2003 | Wienand |
| 2004/0238857 A1 | 12/2004 | Beroz et al. |
| 2006/0001572 A1 | 1/2006 | Gaucher et al. |
| 2006/0049995 A1 | 3/2006 | Imaoka et al. |
| 2006/0067456 A1 | 3/2006 | Ku et al. |
| 2007/0210959 A1 | 9/2007 | Herd et al. |
| 2008/0106460 A1 | 5/2008 | Kurtz et al. |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0153428 A1 | 6/2009 | Rofougaran et al. |
| 2009/0240132 A1 | 9/2009 | Friedman |
| 2009/0315761 A1 | 12/2009 | Walter et al. |
| 2010/0207805 A1 | 8/2010 | Haworth |
| 2011/0299433 A1 | 12/2011 | Darabi et al. |
| 2012/0007765 A1 * | 1/2012 | Margomenos ....... H01Q 21/065 342/175 |
| 2012/0087230 A1 | 4/2012 | Guo et al. |
| 2012/0092284 A1 | 4/2012 | Rofougaran et al. |
| 2012/0116231 A1 | 5/2012 | Liao et al. |
| 2012/0195161 A1 | 8/2012 | Little et al. |
| 2012/0206339 A1 | 8/2012 | Dahl |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2014/0028542 A1 | 1/2014 | Lovitt et al. |
| 2014/0070994 A1 | 3/2014 | Schmalenberg et al. |
| 2014/0142403 A1 | 5/2014 | Brumback et al. |
| 2014/0145883 A1 | 5/2014 | Baks et al. |
| 2014/0324888 A1 | 10/2014 | Xie et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0228010 A1 * | 8/2016 | Kim ...................... A61B 5/021 |
| 2016/0240495 A1 | 8/2016 | Lachner et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 * | 10/2016 | Trotta ..................... G01S 7/006 |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0060254 A1 | 3/2017 | Molchanov et al. |
| 2017/0065184 A1 * | 3/2017 | Barak ................ A61B 5/02438 |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0131395 A1 | 5/2017 | Reynolds et al. |
| 2017/0139036 A1 | 5/2017 | Nayyar et al. |
| 2017/0170947 A1 | 6/2017 | Yang |
| 2017/0176574 A1 | 6/2017 | Eswaran et al. |
| 2017/0192847 A1 | 7/2017 | Rao et al. |
| 2017/0201019 A1 | 7/2017 | Trotta |
| 2017/0212597 A1 | 7/2017 | Mishra |
| 2017/0281015 A1 * | 10/2017 | Tupin, Jr. ............. A61B 5/4848 |
| 2017/0364160 A1 | 12/2017 | Malysa et al. |
| 2018/0046255 A1 | 2/2018 | Rothera et al. |
| 2018/0071473 A1 | 3/2018 | Trotta et al. |
| 2018/0101239 A1 | 4/2018 | Yin et al. |
| 2018/0231651 A1 * | 8/2018 | Charvat .................. G01S 7/282 |

(56) References Cited

U.S. PATENT DOCUMENTS

| | | | | |
|---|---|---|---|---|
| 2018/0239014 | A1* | 8/2018 | McMahon | A61B 5/11 |
| 2019/0006745 | A1 | 1/2019 | Suematsu et al. | |
| 2021/0181297 | A1* | 6/2021 | Zhang | H01L 21/4846 |

FOREIGN PATENT DOCUMENTS

| | | | |
|---|---|---|---|
| CN | 101490578 | A | 7/2009 |
| CN | 101585361 | A | 11/2009 |
| CN | 102788969 | A | 11/2012 |
| CN | 102967854 | A | 3/2013 |
| CN | 103529444 | A | 1/2014 |
| CN | 203950036 | U | 11/2014 |
| DE | 102008054570 | A1 | 6/2010 |
| DE | 102011075725 | A1 | 11/2012 |
| DE | 102014118063 | A1 | 7/2015 |
| GB | 2247799 | A | 3/1992 |
| JP | 2001174539 | A | 6/2001 |
| JP | 2004198312 | A | 7/2004 |
| JP | 2006234513 | A | 9/2006 |
| JP | 2008029025 | A | 2/2008 |
| JP | 2008089614 | A | 4/2008 |
| JP | 2009069124 | A | 4/2009 |
| JP | 2011529181 | A | 12/2011 |
| JP | 2012112861 | A | 6/2012 |
| JP | 2013521508 | A | 6/2013 |
| JP | 2014055957 | A | 3/2014 |
| KR | 20090063166 | A | 6/2009 |
| KR | 20140082815 | A | 7/2014 |
| WO | 2007060069 | A1 | 5/2007 |
| WO | 2013009473 | A2 | 1/2013 |
| WO | 2013118121 | A1 | 8/2013 |
| WO | 2015174879 | A1 | 11/2015 |
| WO | 2016033361 | A1 | 3/2016 |

OTHER PUBLICATIONS

Chen, Xiaolong et al., "Detection and Extraction of Marine Target with Micromotion via Short-Time Fractional Fourier Transform in Sparse Domain," IEEE International Conference on Signal Processing, Communications and Computing, ICSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, pp. 1002-1018.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Dooring Alert Systems, "Riders Matter," http:\\dooringalertsystems.com, printed Oct. 4, 2017, 16 pages.

Filippelli, Mario et al., "Respiratory dynamics during laughter," J Appl Physiol, (90), 1441-1446, Apr. 2001, http://iap.physiology.org/content/jap/90/4/1441.full.pdf.

Fox, Ben, "The Simple Technique That Could Save Cyclists' Lives," https://www.outsideonline.com/2115116/simple-technique-could-save-cyclists-lives, Sep. 19, 2016, 6 pages.

Gu, Changzhan et al., "Assessment of Human Respiration Patterns via Noncontact Sensing Using Doppler Multi-Radar System", Sensors Mar. 2015, 15(3), 6383-6398, doi: 10.3390/s150306383, 17 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Killedar, Abdulraheem "XWR1xxx Power Management Optimizations—Low Cost LC Filter Solution," Application Report SWRA577, Texas Instruments, Oct. 2017, 19 pages.

Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.

Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.

Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi: 10.3390/s150716642, www.mdpi.com/journal/sensors, Jul. 15, 2009, 12 pages.

Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.

Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.

Richards, Mark A., "Fundamentals of Radar Signal Processing," McGraw Hill Electronic Engineering, ISBN: 0-07-144474-2, Jun. 2005, 93 pages.

Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, pp. 815-823.

Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.

Suleymanov, Suleyman, "Design and Implementation of an FMCW Radar Signal Processing Module for Automotive Applications," Master Thesis, University of Twente, Aug. 31, 2016, 61 pages.

Thayananthan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.

Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, pp. 18-34.

Xin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, 11 pages.

* cited by examiner

Die to Die Stacking

Multilayer Chip Stacking

SYSTEM AND METHOD FOR VITAL SIGNAL SENSING USING A MILLIMETER-WAVE RADAR SENSOR

This application is a divisional of U.S. patent application Ser. No. 15/872,701, filed Jan. 16, 2018, which application is hereby incorporated herein by reference.

TECHNICAL FIELD

The present invention relates generally to a system and method for vital signal sensing using a millimeter-wave radar sensor.

BACKGROUND

Applications in the millimeter-wave frequency regime have gained significant interest in the past few years due to the rapid advancement in low cost semiconductor technologies such as silicon germanium (SiGe) and fine geometry complementary metal-oxide semiconductor (CMOS) processes. Availability of high-speed bipolar and metal-oxide semiconductor (MOS) transistors has led to a growing demand for integrated circuits for millimeter-wave applications at 60 GHz, 77 GHz, and 80 GHz and also beyond 100 GHz. Such applications include, for example, automotive radar systems and multi-gigabit communication systems.

In some radar systems, the distance between the radar and a target is determined by transmitting a frequency modulated signal, receiving a reflection of the frequency modulated signal, and determining a distance based on a time delay and/or frequency difference between the transmission and reception of the frequency modulated signal. Accordingly, some radar systems include a transmit antenna to transmit the RF signal, a receive antenna to receive the RF, as well as the associated RF circuitry used to generate the transmitted signal and to receive the RF signal. In some cases, multiple antennas may be used to implement directional beams using phased array techniques. A MIMO configuration with multiple chipsets can be used to perform coherent and non-coherent signal processing, as well.

SUMMARY

A system includes a millimeter-wave radar sensor disposed on a circuit board, a plurality of antennas coupled to the millimeter-wave radar sensor and disposed on the circuit board, and a processing circuit coupled to the millimeter-wave radar sensor and disposed on the circuit board. The processing circuit is configured to determine vital signal information based on output from the millimeter-wave radar sensor.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale. To more clearly illustrate certain embodiments, a letter indicating variations of the same structure, material, or process step may follow a figure number.

DETAILED DESCRIPTION OF ILLUSTRATIVE EMBODIMENTS

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, a system and method for vital signal sensing using a millimeter-wave radar sensor. The invention may also be applied to other RF-based systems and applications that detect and identify the presence of one or more objects based on motion of the object.

In embodiments of the present invention, a millimeter-wave based radar sensor is used to measure vital signal information such as pulse rate. Such a millimeter-wave based radar sensor may be mounted to a smartphone, a wristwatch, a chest strap or other device. In various embodiments, the relevant vital signal is determined by using high response "range gate" measurements that may be determined, for example, by taking a fast Fourier transform (FFT) of down-converted frequency modulated continuous wave (FMCW) measurements from the millimeter-wave based radar sensor. These range gate measurements are then filtered determine the relevant vital signal. Such filtering may be adaptively calibrated to compensate for irregularities in the physical coupling between the millimeter-wave based radar sensor and the body being measured. In some embodiments, the motion of the millimeter-wave based radar sensor with respect to the body being measured is compensated for by tracking shifts in the high response range gates and stitching together measurements from multiple range gates to form the basis for the vital signal measurement.

Advantages of embodiment vital signal sensing systems may include the ability to perform accurate vital signal measurements in the presence of relative motion between the millimeter-wave based radar sensor and the body being measured. Such advantages are particularly relevant for vital sensing applications in which heartbeat is measured on a human being in motion, such as someone who is exercising.

Figure 1A:
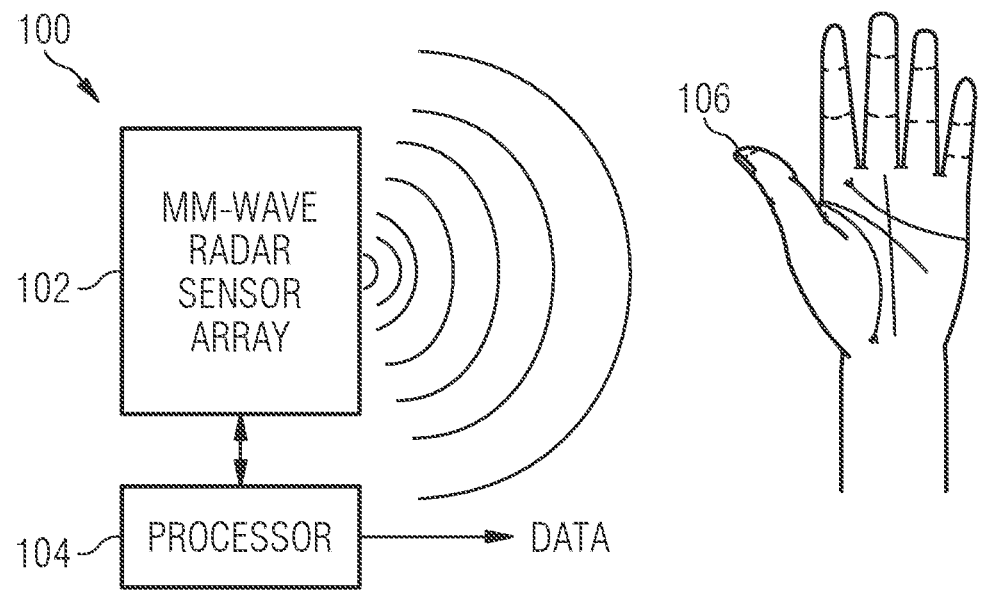
FIG. 1A illustrates an embodiment vital signal measurement system.

FIG. 1A illustrates a block diagram of radar-based vital signal measuring system 100. As shown, radar-based vital signal measuring system 100 includes a millimeter-wave radar sensor 102, and a processor 104 that controls the operation of millimeter-wave radar sensor 102 and performs various radar signal processing operations on the data produced by millimeter-wave radar sensor 102. During operation, millimeter-wave radar sensor 102 transmits millimeter-wave RF signals that are reflected by object 106. While object 106 is depicted as a human hand, it should be understood that object 106 may be any body from which a vital signal is to be measured. The reflected signals are received by millimeter-wave radar sensor 102, converted to a digital representation, and processed by processor 104 to determine, for example, a vital signal produced by object 106, such as a pulse rate. The result of this processing produces various data (represented by signal DATA) indicative of the measured vital signals.

Figure 1B:
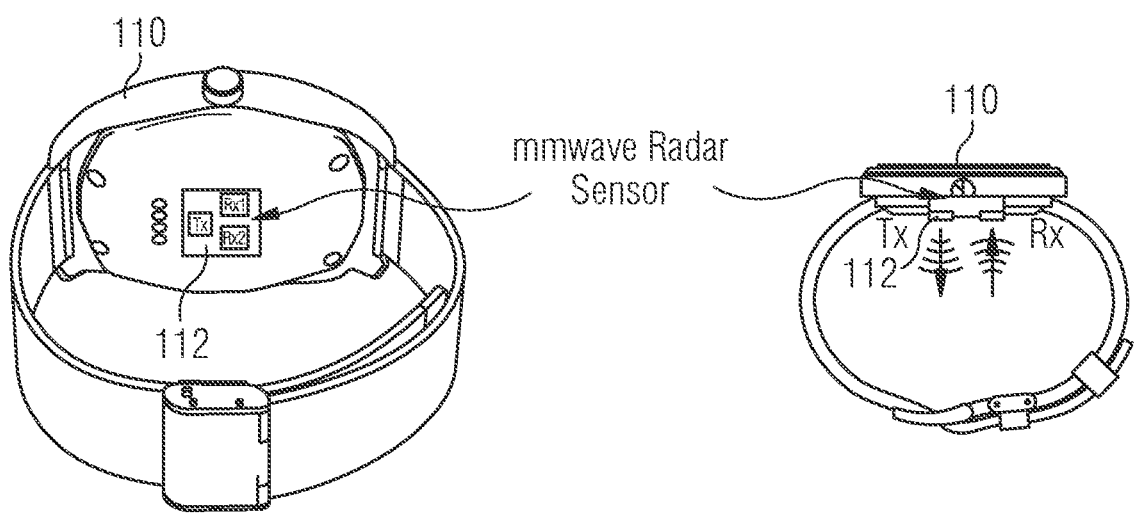
FIGS. 1B, 1C and 1D illustrate a smart watch, a chest strap, and a smart phone that incorporate embodiment vital signal measurement systems.
Figure 1C:
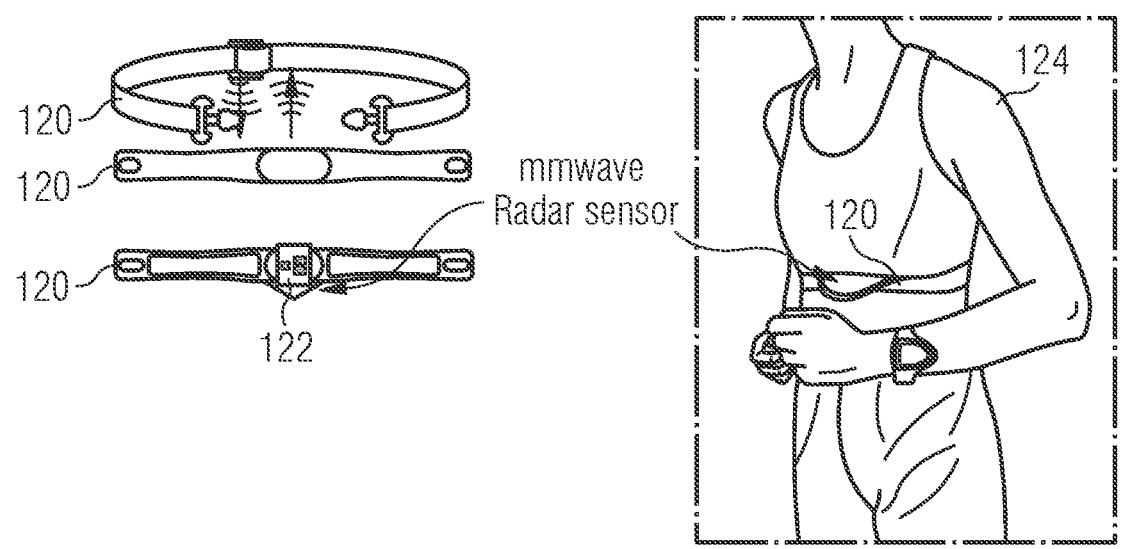
Figure 1D:

FIGS. 1B, 1C and 1D illustrate example vital signal sensing configurations. For example, FIG. 1B illustrates a rear-view and a side-view of a wristwatch no that includes millimeter-wave radar sensor 112. As shown, millimeter-wave radar sensor 112 includes one transmit antenna Tx and two receive antennas Rx1 and Rx2. Alternatively, other antenna configurations may be used. During operation, millimeter-wave radar sensor 112 transmits millimeter wave radar signals to a user's wrist and determines, for example, a heart rate based on the reflected RF signal.

FIG. 1C illustrates various views of a chest strap 120 that includes millimeter-wave radar sensor 122. During operation, millimeter-wave radar sensor 112 transmits millimeter wave radar signals to the chest of user 124 and determines a heart rate of user 124 by analyzing radar signals reflected from the chest of user 124.

FIG. 1D illustrates a rear view of a smart phone 130 on which a millimeter-wave radar sensor 132 is mounted. As shown, millimeter-wave radar sensor 132 includes one transmit antenna Tx and one receive antenna Rx. Alternatively, other antenna configurations may be used. During operation, millimeter-wave radar sensor 132 transmits millimeter wave radar signals to any portion of the body to which the rear portion of smartphone 130 is facing, and determines for example, a heart rate based on the reflected RF signal. The results of the vital signal measurement may be shown on the screen of 130 via a software application or graphical user interface 134.

It should be understood that wristwatch no, chest strap 120 and smartphone 130 shown in FIGS. 1B, 1C and 1D, respectively, are just three specific embodiment examples of many possible embodiment system configuration that employ millimeter-wave radar based vital signal sensing.

Figure 2A:
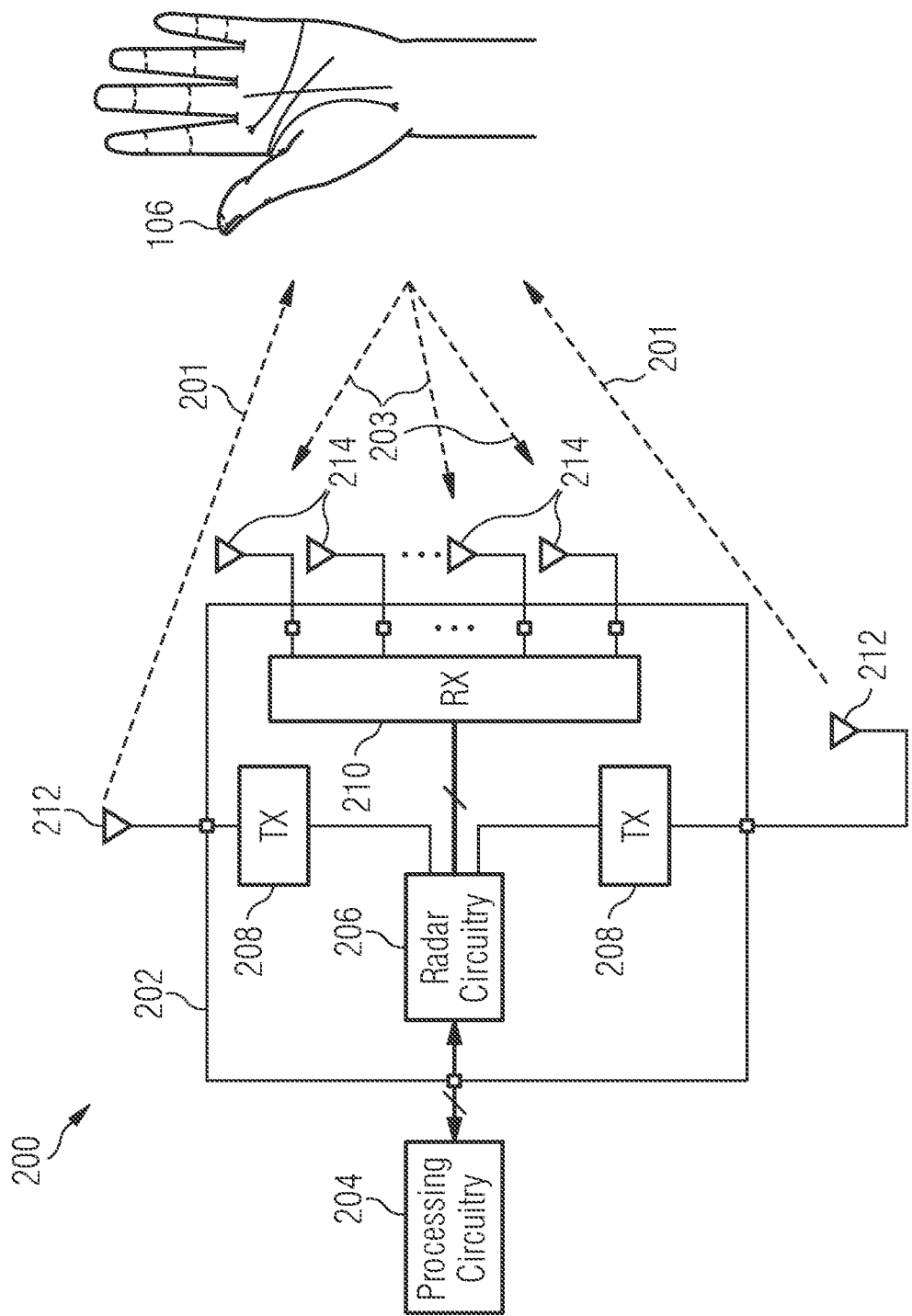
FIG. 2A illustrates a block diagram of an embodiment millimeter-wave radar sensor.

FIG. 2A illustrates a block diagram of a millimeter-wave radar sensor system 200 that may be used to implement millimeter-wave radar sensor circuits in the various disclosed embodiments. Millimeter-wave radar sensor system 200 includes millimeter-wave radar sensor circuit 202 and processing circuitry 204. Embodiment millimeter-wave radar sensor circuits may be implemented, for example, using a two-dimensional millimeter-wave phase-array radar that performs measurements on object 106. The millimeter-wave phase-array radar transmits and receives signals in the 20 GHz to 122 GHz range. Frequencies outside of this range may also be used. In some embodiments, millimeter-wave radar sensor circuit 202 operates as a frequency modulated continuous wave (FMCW) radar sensor having multiple transmit and receive channels. Alternatively, other types of radar systems may be used such as pulse radar, continuous wave (CW) radar, frequency modulated continuous wave (FMCW) radar, and non-linear frequency modulated (NLFM) radar to implement millimeter-wave radar sensor circuit 202.

Millimeter-wave radar sensor circuit 202 transmits and receives radio signals for determining vital signals of object 106. For example, millimeter-wave radar sensor circuit 202 transmits incident RF signals 201 and receives RF signals 203 that are a reflection of the incident RF signals from object 106. The received reflected RF signals 203 are down converted by millimeter-wave radar sensor circuit 202 to determine beat frequency signals. These beat frequency signals may be used to determine information such as the location and motion of object 106. In the specific example of FMCW radar, the beat frequency is proportional to the distance between millimeter-wave radar sensor circuit 202 and the object being sensed.

In various embodiments, millimeter-wave radar sensor circuit 202 is configured to transmit incident RF signals 201 toward object 106 via transmit antennas 212 and to receive reflected RF signals 203 from object 106 via receive antennas 214. Millimeter-wave radar sensor circuit 202 includes transmitter front-end circuits 208 coupled to transmit antennas 212 and receiver front-end circuit 210 coupled to receive antennas 214.

During operation, transmitter front-end circuits 208 may transmit RF signals toward object 106 simultaneously or individually using beamforming depending on the phase of operation. While two transmitter front-end circuits 208 are depicted in FIG. 2A, it should be appreciated that millimeter-wave radar sensor circuit 202 may include less than or greater than two transmitter front-end circuits 208. Thus, in various embodiments, the number of transmitters can be extended to n×m. Each transmitter front-end circuit 208 includes circuitry configured to produce the incident RF signals. Such circuitry may include, for example, RF oscillators, upconverting mixers, RF amplifiers, variable gain amplifiers, filters, transformers, power splitters, and other types of circuits.

Receiver front-end circuit 210 receives and processes the reflected RF signals from object 106. As shown in FIG. 2A, receiver front-end circuit 210 is configured to be coupled to four receive antennas 214, which may be configured, for example, as a 2×2 antenna array. In alternative embodiments, receiver front-end circuit 210 may be configured to be coupled to greater or fewer than four antennas, with the resulting antenna array being of various n×m dimensions depending on the specific embodiment and its specifications. Receiver front-end circuit 210 may include, for example, RF oscillators, upconverting mixers, RF amplifiers, variable gain amplifiers, filters, transformers, power combiners and other types of circuits.

Radar circuitry 206 provides signals to be transmitted to transmitter front-end circuits 208, receives signals from receiver front-end circuit 210, and may be configured to control the operation of millimeter-wave radar sensor circuit 202. In some embodiments, radar circuitry 206 includes, but is not limited to, frequency synthesis circuitry, up-conversion and down-conversion circuitry, variable gain amplifiers, analog-to-digital converters, digital-to-analog converters, digital signal processing circuitry for baseband signals, bias generation circuits, and voltage regulators.

Radar circuitry 206 may receive a baseband radar signal from processing circuitry 204 and control a frequency of an RF oscillator based on the received baseband signal. In some embodiments, this received baseband signal may represent a FMCW frequency chirp to be transmitted. Radar circuitry 206 may adjust the frequency of the RF oscillator by applying a signal proportional to the received baseband signal to a frequency control input of a phase locked loop. Alternatively, the baseband signal received from processing circuitry 204 may be upconverted using one or more mixers. Radar circuitry 206 may transmit and digitize baseband signals via a digital bus (e.g., a USB bus), transmit and receive analog signals via an analog signal path, and/or transmit and/or receive a combination of analog and digital signals to and from processing circuitry 204.

Processing circuitry 204 acquires baseband signals provided by radar circuitry 206 and formats the acquired baseband signals for transmission to an embodiment signal processing unit. These acquired baseband signals may represent beat frequencies, for example. In some embodiments, processing circuitry 204 includes a bus interface (not shown) for transferring data to other components within the occupancy detection system. Optionally, processing circuitry 204 may also perform signal processing steps used by embodiment occupancy detection systems such as a fast Fourier transform (FFT), a short-time Fourier transform (STFT), macro-Doppler analysis, micro-Doppler analysis, vital sign analysis, object classification, machine learning, and the like. In addition to processing the acquired baseband signals, processing circuitry 204 may also control aspects of millimeter-wave radar sensor circuit 202, such as controlling the transmissions produced by millimeter-wave radar sensor circuit 202.

The various components of millimeter-wave radar sensor system 200 may be partitioned in various ways. For example, millimeter-wave radar sensor circuit 202 may be implemented on one or more RF integrated circuits (RFICs), antennas 212 and 214 may be disposed on a circuit board, and processing circuitry 204 may be implemented using a processor, a microprocessor, a digital signal processor and/or a custom logic circuit disposed on one or more integrated circuits/semiconductor substrates. Processing circuitry 204 may include a processor that executes instructions in an executable program stored in a non-transitory computer readable storage medium, such as a memory to perform the functions of processing circuitry 204. In some embodiments, however, all or part of the functionality of processing circuitry 204 may be incorporated on the same integrated circuit/semiconductor substrate on which millimeter-wave radar sensor circuit 202 is disposed.

In some embodiments, some or all portions of millimeter-wave radar sensor circuit 202 may be implemented in a package that contains transmit antennas 212, receive antennas 214, transmitter front-end circuits 208, receiver front-end circuit 210, and/or radar circuitry 206. In some embodiments, millimeter-wave radar sensor circuit 202 may be implemented as one or more integrated circuits disposed on a circuit board, and transmit antennas 212 and receive antennas 214 may be implemented on the circuit board adjacent to the integrated circuits. In some embodiments, transmitter front-end circuits 208, receiver front-end circuit 210, and radar circuitry 206 are formed on a same radar front-end integrated circuit (IC) die. Transmit antennas 212 and receive antennas 214 may be part of the radar front-end IC die, or may be implemented as separate antennas disposed over or adjacent to the radar front-end IC die. The radar front-end IC die may further include conductive layers, such as redistribution layers (RDLs), used for routing and/or for the implementation of various passive or active devices of millimeter-wave radar sensor circuit 202. In an embodiment, transmit antennas 212 and receive antennas 214 may be implemented using the RDLs of the radar front-end IC die.

Figure 2B:
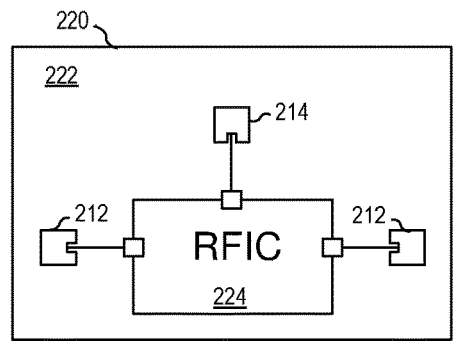
FIGS. 2B and 2C illustrate plan views of embodiment millimeter-wave radar sensor circuits.

FIG. 2B illustrates a plan view of millimeter-wave radar sensor circuit 220 that may be used to implement millimeter-wave radar sensor circuit 202. As shown, millimeter-wave radar sensor circuit 220 is implemented as an RFIC 224 coupled to transmit antennas 212 and receive antenna 214 implemented as patch antennas disposed on or within substrate 222. In some embodiments, substrate 222 may be implemented using a circuit board on which millimeter-wave radar sensor circuit 202 is disposed and on which transmit antennas 212 and receive antennas 214 are implemented using conductive layers of the circuit board. Alternatively, substrate 222 represents a wafer substrate on which one or more RDLs are disposed and on which transmit antennas 212 and receive antennas 214 are implemented using conductive layers on the one or more RDLs.

Figure 2C:
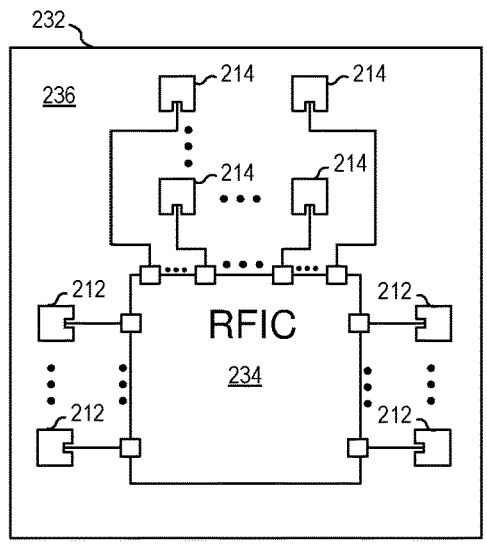

FIG. 2C illustrates a plan view of millimeter-wave radar sensor circuit 232 that includes an array of transmit antennas 212 and an array of receive antennas 214 coupled to RFIC 234 disposed on substrate 236. In various embodiments, transmit antennas 212 may form an array of m antennas and receive antennas 214 may form an array of n antennas. Each of the m transmit antennas 212 is coupled to a corresponding pin on RFIC 234 and coupled to a corresponding transmit circuit within RFIC 234; and each of the n receive antennas 214 is coupled to a corresponding pin on RFIC 234 and coupled to a corresponding receive circuit within RFIC 234. In various embodiments, the array of transmit antennas 212 and the array of receive antennas 214 may be implemented as a uniform array or a linear array of any dimension. It should be appreciated that the implementations of FIGS. 2B and 2C are just two examples of the many ways that embodiment millimeter-wave radar sensor circuits could be implemented.

Figure 2D:
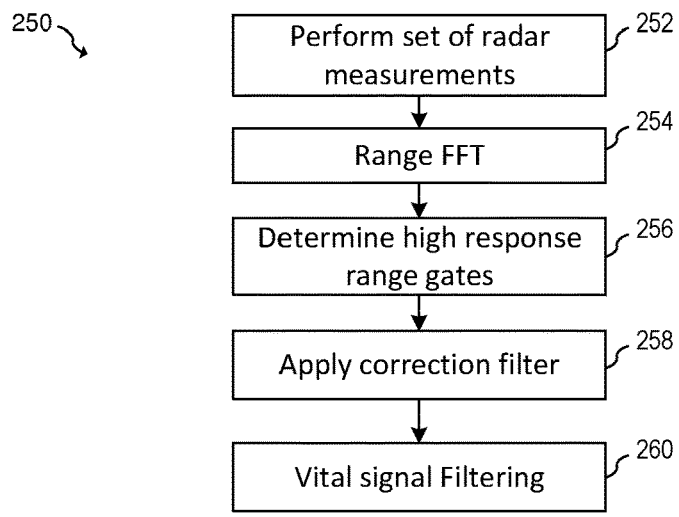
FIG. 2D illustrates a block diagram of an embodiment vital signal sensing method.

FIG. 2D illustrates a method 250 of performing vital signal measurement that may be used in conjunction with an embodiment millimeter-wave radar sensor circuit such as millimeter-wave radar sensor circuit 202, 220, or 232 described above with respect to FIGS. 2A, 2B and 2C. In step 252, the millimeter-wave sensor circuit performs a set of radar measurements, such as FMCW radar measurements. In step 254 an FFT is taken of the baseband representation of these measurements, which are in the form of beat frequencies. Such an FFT may be referred to as a "range FFT" because each bin of the resulting FFT represents energy reflected by an object at a particular range or distance. In alternative embodiments, other transforms may be used besides an FFT, such as a discrete cosine transform (DCT), Short Time Fractional Fourier Transform (STFrFT), z-transform or other transform types known in the art. In step 256, the highest amplitude FFT bins or "range gates" are determined. These high response range gates represent the distance to the largest objects in the range of the millimeter-wave radar sensor. Thus, in various embodiments in which the monitored object is a portion of the human body that includes arteries or portions of the body that move during due to blood flow, the motion of these high response range gates may contain information related to the monitored object's heart rate. In some embodiments, determining the high response range gates includes determining which range gates of a first set of range gate measurements have a higher peak-to-average ratio or a higher amplitude compared to the mean amplitude. For example, in some embodiments, the peak-to-average ratio is greater than 1.3 and/or the amplitude is twice the mean amplitude. Alternatively, difference peak-to-average ratios and amplitudes may be used.

In step 258 a correction filter is applied to the high response range gates. This correction filter may provide equalization and/or compensate for losses or distortion in the physical coupling between the millimeter-wave radar sensor and the target. In some embodiments, this correction filter is an adaptive filter, such as an adaptive Finite Impulse Response (FIR) filter, that is calibrated according to a particular use case. For example, the correction filter may be calibrated to correct for the coupling between a millimeter-wave radar sensor mounted in a smart-watch or wrist band and the user's wrist. Another correction filter may be calibrated to correct for the coupling between the millimeter-wave radar sensor mounted in a chest strap or and the user's chest. The correction filter may be calibrated to correct for the coupling between the millimeter-wave radar sensor and other mounting or use scenarios. In some embodiments this correction filter may be calibrated using an adaptation algorithm during the manufacture of the vital signal sensing device and/or during a user calibration of the vital signal sensing device, as will be described below. In some embodiments, the particular use case (e.g., wrist strap, chest strap, etc.) may be automatically detected base on the set of radar measurements performed in step 252 and the applicable correction filter (or correction filter coefficients) are selected based on the particular use case. In step 260, the output of the correction filter is further filtered by a vital signal filter to extract vital signal information such as heart beat signals.

Figure 3A:
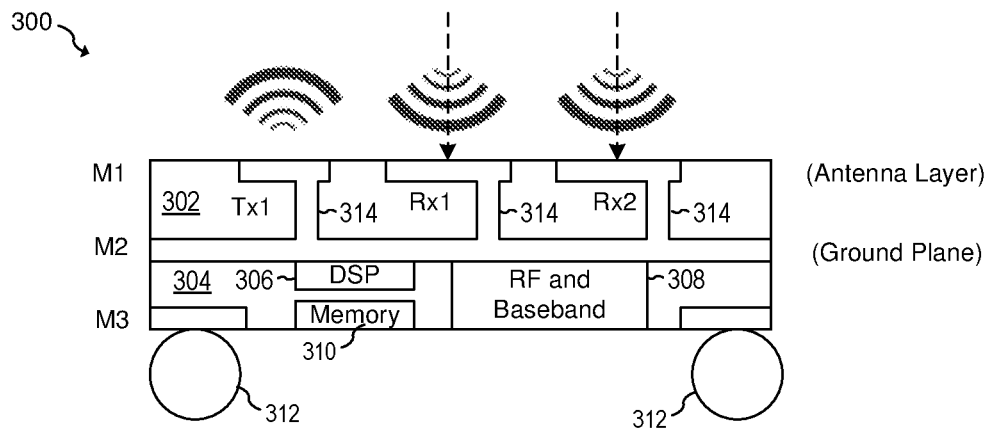
FIGS. 3A, 3B, 3C, 3D and 3E illustrate radar sensor circuit boards according to embodiments of the present invention.

FIGS. 3A to 3E illustrate side views of various embodiment substrate configurations that may be used to implement radar sensors for embodiment millimeter-wave radar based vital signal sensing systems, such as radar sensors 110, 112, 122 and 132 shown in FIGS. 1A, 1B, 1C and 1D, respectively. In accordance with one embodiment, FIG. 3A illustrates a side view of a radar sensor circuit board 300 that includes three conductive layers, M1, M2 and M3 and two laminate layers 302 and 304. As shown, conductive layer M1 is used as an antenna layer and is used to implement transmit antenna TX1 and receive antennas RX1 and RX2. Conductive layer M2 is used, for example, as a ground plane, and conductive layer M3 is used to make contact with solder balls 312. In the illustrated embodiment, RF and baseband integrated circuit 308, digital signal processor (DSP) integrated circuit 306 and memory integrated circuit 310 are embedded within laminate layer 304. Integrated circuits 308 and 310 may be embedded in a laminate using an embedding process known in the art. For example, the embedding process may include making a cavity in the laminate and placing the integrated circuit therein. The process may also include growing a substrate after the integrated circuits are embedded. Contact between RF and baseband integrated circuit 308 and antennas Tx1, Rx1 and Rx2 is made using vias 314. In alternative embodiments, laminate layers 302 and 304 may be implemented differently. For example, layers 302 and 304 may be implemented using low temperature co-fired ceramic (LTCC) substrates.

In various embodiments, RF and baseband integrated circuit 308 includes the RF and analog components of a millimeter-wave radar sensor including the RF/radar front end, the various frequency generation circuitry, as a one or more oscillators and phase locked loops (PLLS), upconversion and downconversion circuitry, baseband circuitry and various support circuitry. RF and baseband integrated circuit 308 may also include analog-to-digital converters that convert analog signals derived from the received radar signal to the digital domain in the form of raw data.

DSP integrated circuit 306 is coupled to RF and baseband integrated circuit 308 and is configured to receive the raw data produced by RF and baseband integrated circuit 308. In various embodiments, DSP integrated circuit 306 is configured to perform embodiment vital signal analysis and machine learning functions described below. DSP integrated circuit 306 may also be configured to perform calibration, adaptive filtering and signal processing algorithms that support the operation of the embodiment radar system. DSP integrated circuit 306 may be implemented using digital signal processing circuitry and/or other processing circuitry known in the art. DSP integrated circuit 306 also enables the execution of various computationally intensive algorithms within the radar system, which reduces the computational loading of and the amount of data exchanged with external application processors.

Memory integrated circuit 310 may include volatile and/or non-volatile memory on which configuration data and intermediate calculations data are stored. In some embodiments, memory integrated circuit 310 may be configured to store several days, months or years worth of vital signal data in order to support the various machine learning algorithms implemented by DSP integrated circuit 306. In addition, statistics may be generated using the data stored in memory circuit 310. Memory integrated circuit 310 may also help support the storage of data for an external application processor in addition to supporting operation of DSP integrated circuit 306.

In some embodiments, the conductive layers M1, M2 and M3 may be formed from a metal foil, metal layer, or metallization that has been laminated to a laminate layer. In one embodiment, the conductive layers comprise copper (Cu). In some embodiments, the conductive layers comprise other conductive materials such as silver (Ag) and aluminum (Al). In some embodiments, the conductive layers may comprise different conductive materials.

The laminate layers may separate the conductive layers and provide structural support for radar sensor circuit board 300. In various embodiments, the laminate layers are implemented using an insulator material. For example, a low-loss high frequency material such as a woven glass reinforced hydrocarbon ceramic and/or polytetrafluoroethylene (PTFE) may be used. In some embodiments, the laminate layers comprise a pre-impregnated composite material (PPG). One or more of the laminate layers may be commercial laminate material manufactured with copper cladding on one or both surfaces. In some embodiments, all laminate material layers may comprise the same insulator material, while in other embodiments, different laminate material layers may be implemented using different insulating materials.

One type of laminate material that may be used to form the conductive layers and laminate layers in radar sensor circuit board 300 is copper clad laminate. Sheets of copper clad laminate material may be fabricated as single-sided or double-sided copper clad sheets. During the fabrication process, copper sheets may be placed on one or both sides of the laminate material. Some combination of heat and pressure may then be applied to facilitate attachment of the copper sheets to the laminate material.

A conductive layer on a surface of a laminate layer may be an electrodeposited (ED) foil or a rolled foil, for example. A rolled foil sheet may be produced by repeatedly feeding the foil sheet through rollers to evenly reduce the thickness of the foil sheet. ED foil may be more rigid and have a different grain structure. In contrast, rolled foil may be smooth and flexible. In some cases, rolled foil may be advantageous in RF applications, due to decreased surface roughness.

One or more vias 314 connect the first conductive layer M1 and the second conductive layer M2 and/or the RF and baseband integrated circuit. For example, prior to attaching laminate layer 302 to laminate layer 304, one or more vias 314 may be formed as through substrate vias (TSVs) passing through laminate layer 302 from the second conductive layer M2 on the back side surface of laminate layer 302 to an opposing surface of laminate layer 302. Vias 314 may be exposed at the opposing surface such that electrical contact is made with third conductive layer M3 upon attachment laminate layer 302 to laminate layer 304.

Figure 3B:
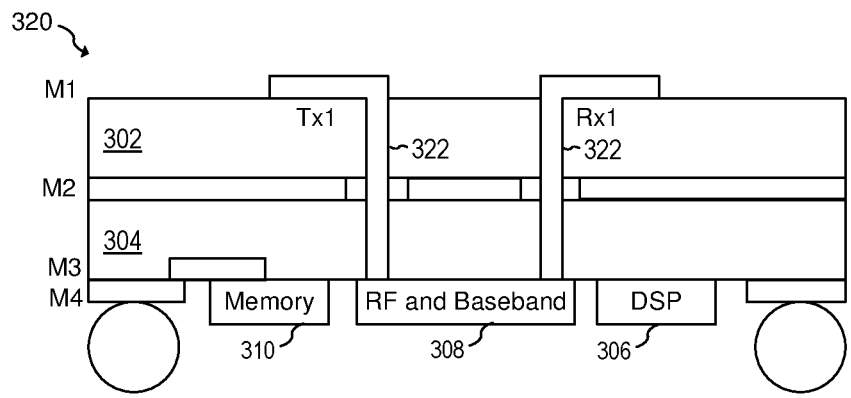

FIG. 3B illustrates a side view of a radar sensor circuit board 320 that includes three conductive layers, M1, M2, M3 and M4 and two laminate layers 302 and 304. Conductive layer M1 is used as an antenna layer to implement transmit antenna TX1 and receive antenna RX1. Conductive layer M2 is used, for example, as a ground plane and/or an interconnect layer, and conductive layer M3 is used as an interconnect layer. Conductive layer M4 is used to make contact with solder balls 312. In the illustrated embodiment, RF and baseband integrated circuit 308, digital signal processor integrated circuit 306 and memory integrated circuit 310 are mounted on the bottom surface of laminate layer 304. Contact between RF and baseband integrated circuit 308 and antennas Tx1 and Rx1 is made using vias 322. Integrated circuits 306 and 308 and 310 may be attached to laminate layer 304 using chip-on-board methods known in the art.

Figure 3C:
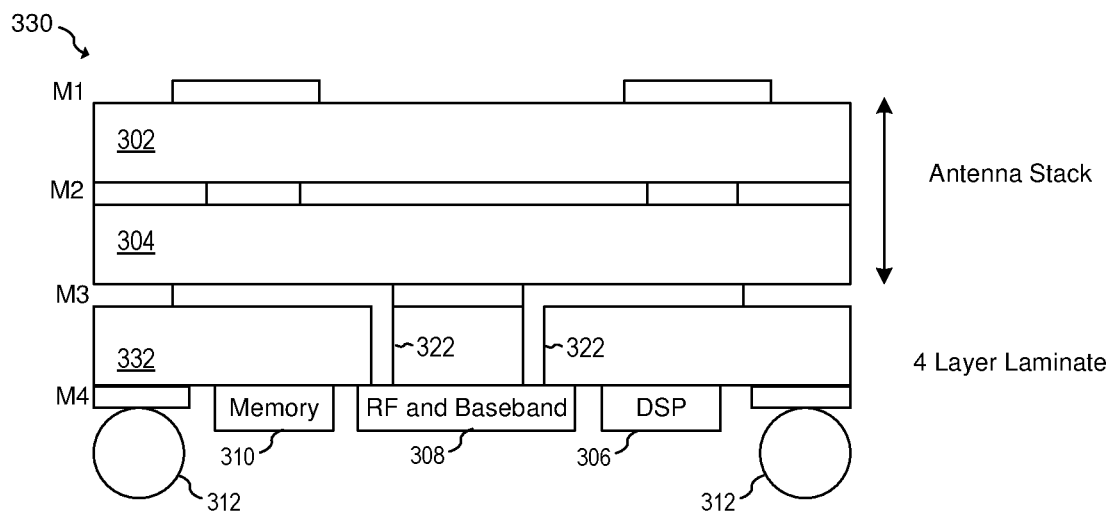

FIG. 3C illustrates a side view of a radar sensor circuit board 330 that utilizes a four layer laminate structure having four conductive layers M1, M2, M3 and M4 and three laminate layers 302, 304 and 332. Additional laminate layer 332 may be constructed in a similar manner using similar materials as laminate layers 302 and 304 described above. In the embodiment of FIG. 3C, conductive layers M1, M2 and laminate layer 302 and 304 are used to implement an antenna stack. In an embodiment antenna stack, conductive layer M4 functions as a ground plane, conductive layer M3 functions as a feeding line, conductive layer M2 functions as a ground plane, and conductive layer M1 functions as a patch antenna. Conductive layer M3 may include a slot to couple the energy of the feeding line to the patch antenna of conductive layer M1. Laminate layer 302 define the bandwidth of antenna and laminate layers 304 and 332 may be selected to match the feeding line in M3. In some implementations, laminate layers 304 and 332 are selected to provide an optimum match. As shown, RF and baseband integrated circuit 308, digital signal processor integrated circuit 306 and memory integrated circuit 310 are mounted on the bottom surface of laminate layer 332. Contact between RF and baseband integrated circuit 308 and the feeding line of the antenna is made using vias 322.

Figure 3D:
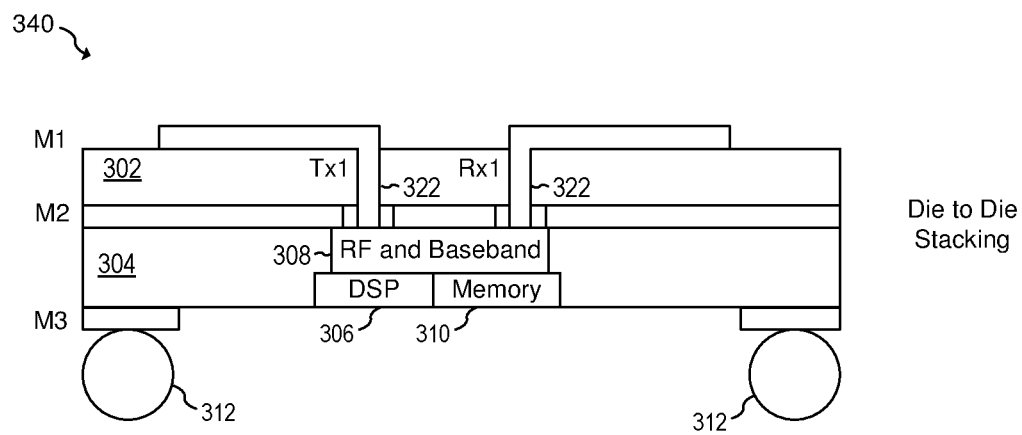

FIG. 3D illustrates a side view of a radar sensor circuit board 340 that utilizes three conductive layers M1, M2 and M3 and two laminate layers 302 and 304 and die to die stacking. As shown, RF and Baseband integrated circuit 308 is stacked on top of DSP integrated circuit 306 and memory integrated circuit 310 within laminate layer 304. Contact between RF and baseband integrated circuit 308 and transmit antenna Tx1 and receive antenna Rx1 is made using vias 322.

Figure 3E:
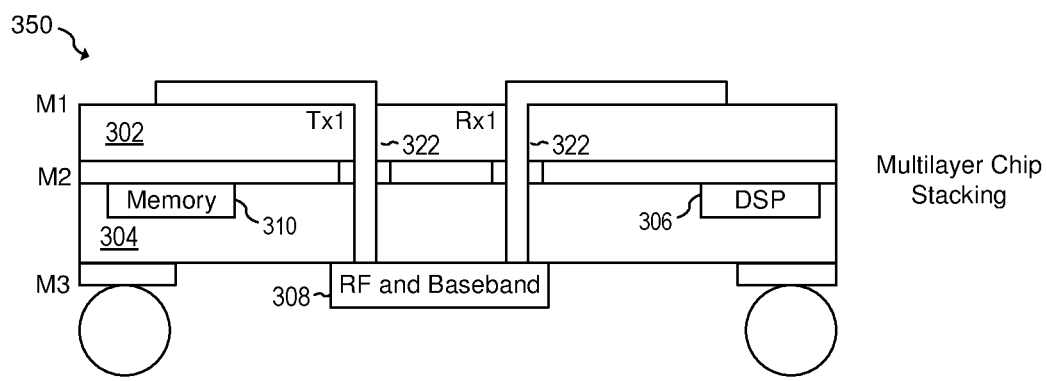

FIG. 3E illustrates a side view of a radar sensor circuit board 350 that utilizes three conductive layers M1, M2 and M3 and two laminate layers 302 and 304 and multilayer chip stacking. As shown, RF and Baseband integrated circuit 308 is mounted on the bottom surface of laminate layer 304. Memory integrated circuit 310 and DSP integrated circuit 306 are disposed within the top surface of laminate layer 304. Contact between RF and baseband integrated circuit 308 and transmit antenna Tx1 and receive antenna Rx1 is made using vias 322.

Figure 4A:
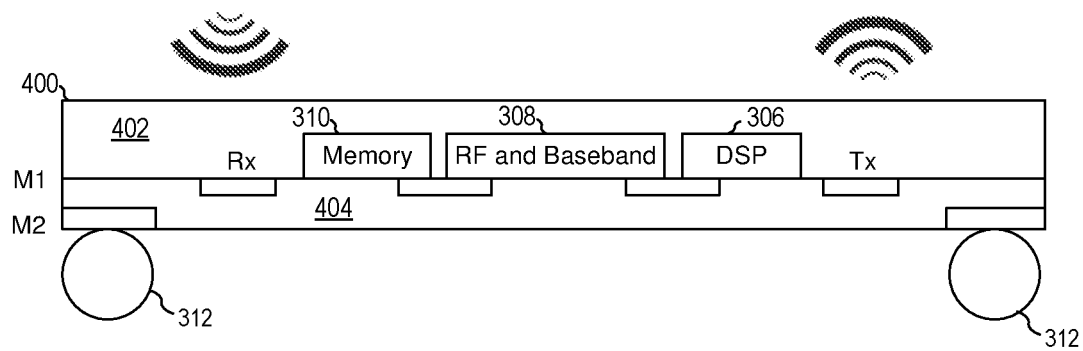
FIGS. 4A and 4B illustrate an embodiment radar sensor implemented using a waver level package construction.

FIG. 4A illustrates a cross-sectional view of an embodiment RF system/antenna package 400. In a specific embodiment directed toward an embedded wafer level ball grid array (eWLB) package, RF system/antenna package 420 includes a molding material layer 402 that is and a redistribution layer (RDL) 404 disposed beneath molding material. In some embodiments, molding material layer 402 is composed of mold and laminate materials and is between about 200 μm and 600 μm thick, and RDL 404 is composed of an conducting material, such as copper and is between about 5 μm and about 15 μm thick. As shown, integrated circuit die 306, 308 and 310 are disposed in a single layer within a cavity within molding material 402. Receive patch antenna Rx, transmit patch antenna Tx are located in the fan out area of the eWLB package, and connections between integrated circuit die 306, 308 and 310 are made in a first layer of metal M1 at a first surface of (RDL) 404. In embodiments, RF system/antenna package 400 may include further conductive layers used for routing and/or for the implementation of various passive devices within the substrate of the package. For example a second level of metal M2 on the opposite side of RDL 404 from first level of metal M1 is used to made contact to solder balls 312. It should be understood that the specific dimensions detailed herein are just examples. In alternative embodiments of the present invention, other dimensions could be used. In further alternative embodiments of the present invention, other package types such as a BGA or Advanced Thin Small Leadless ATSPL package may also be used.

Figure 4B:
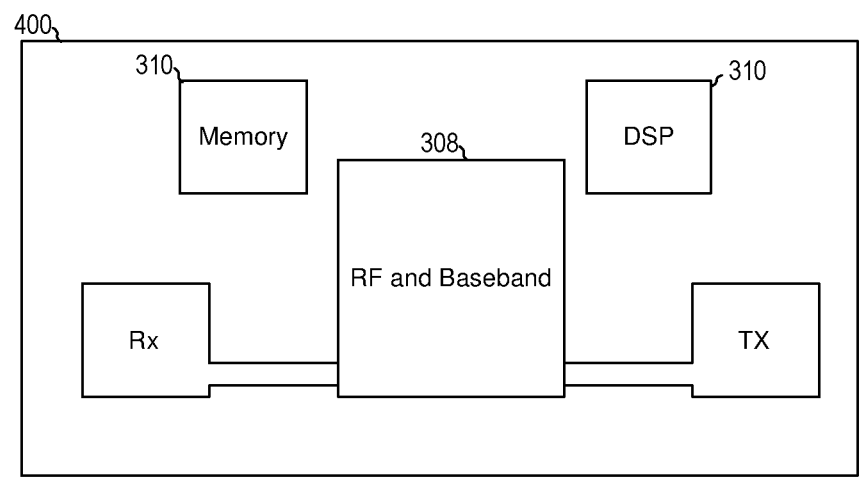

FIG. 4B illustrates a plan view of embodiment radar sensor 400. As shown, antennas Rx and Tx as implemented as patch antennas in metal layer M1. It should be understood that the embodiment shown in FIG. 4B is just one example of the many possible ways the various components can be arranged. In alternative embodiments RF and Baseband integrated circuit 308, memory integrated circuit 310, DSP integrated circuit 306, transmit antenna Tx and receive antenna Rx may be arranged differently.

It should be appreciated that the radar sensor circuit board examples shown in FIGS. 3A to 3E and FIGS. 4A and 4B are just a few of the many possible configurations for implementing embodiment radar sensor circuit boards. For example, while FIG. 3B-3E and FIGS. 4A and 4B each show a single transmit antenna and a signal receive antenna, in alternative embodiments, different numbers of receive and transmit antennas may be implemented depending on the particular requirements of the radar system. In some embodiments, the number and transmit and/or receive channels and antennas may be increased in order to implement beam steering. By using beam steering, the radar beam may be directed in a particular direction. This may be used, for example, to direct the radar beam toward fine veins and arteries in order to perform more accurate and precise vital signal measurements.

Figure 5:
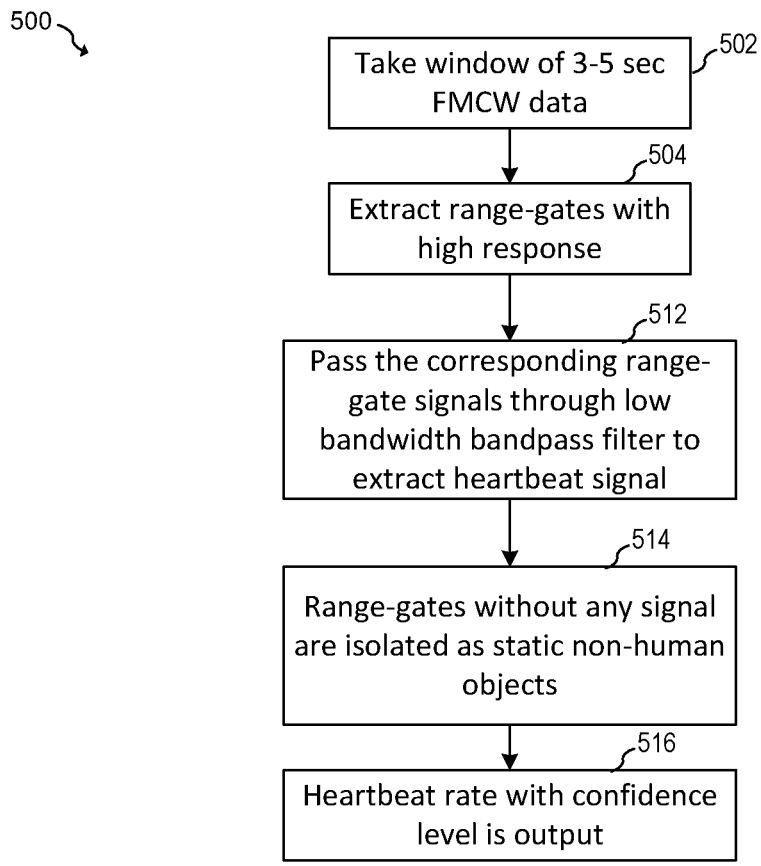
FIG. 5 illustrates a flowchart of an embodiment method of millimeter-wave based vital signal detection.

FIG. 5 illustrates a flowchart of an embodiment method 500 of millimeter-wave based vital signal detection. In step 502, baseband FMCW radar data is collected over a sampling window. In some embodiments, this window is between about 3 seconds and 5 seconds in length, however, other window lengths may be used. The downconverted FMCW radar data may be in the form of digitized time samples that form a periodic signal having an instantaneous frequency proportional to a distance between the millimeter wave radar sensor and a detected object. In step 504, range gates with high responses are extracted from the windowed FMCW data. In various embodiments, this may be accomplished by taking an FFT or other transform of the FMCW data and determining which frequency bins have a highest response. Since each frequency represents a "range gate" or determined distance, the highest response range gate responses represent the distance of the user whose vital signals are to be measured. In the case of most wearable devices in which only one target is to be tracked, there will likely be either a single high response range gate or a cluster of high response range gates that represent the distance from the millimeter-wave radar sensor to the nearest target. These high response range gates may shift over time due to the relative motion between the millimeter-wave radar sensor and the user. Thus, in some embodiments, the identity of the high response range gates are tracked over time as described in further detail below.

Once the high response range gates are extracted in step 504, the motion represented by these high response range gates may be analyzed to determine vital signals such as heart rate. For example, in step 512, the high response range gate signals are bandpass filtered to extract a heartbeat signal. In some embodiments, the bandwidth of the heart bandpass filter may be between about 0.8 Hz and about 3.33 Hz. Bandwidths outside of these ranges may also be used depending on the particular embodiment and its specifications. In step 514, identified range gates in which no signals are detected are identified as static non-human objects and in step 516, a heart rate is derived from the filtering operation of step 512. In some embodiments, a confidence level of the heart rate may also be derived as explained below.

Figure 6:
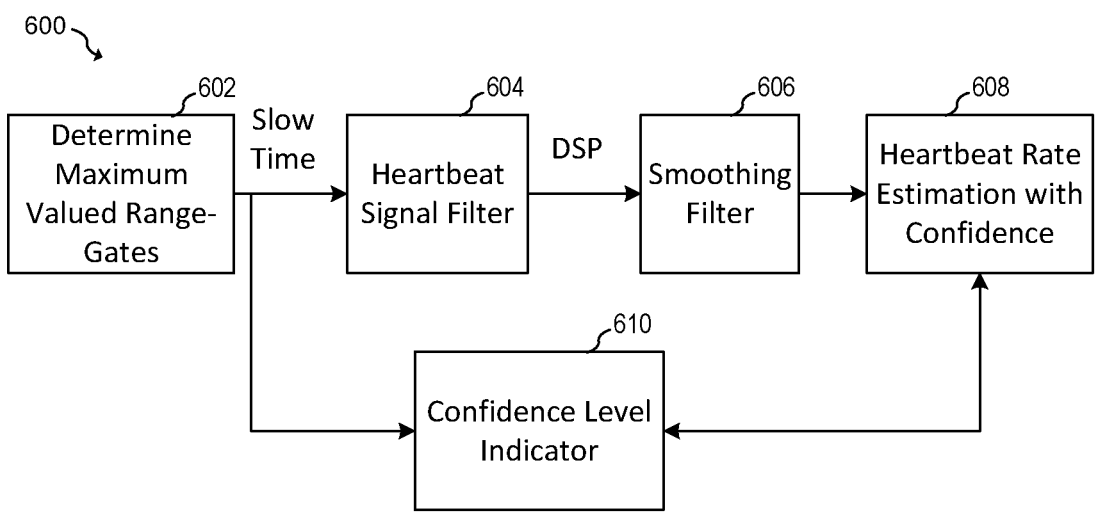
FIG. 6 illustrates an embodiment heart rate detection processing block diagram.

FIG. 6 illustrates a heart rate detection processing block diagram 60o according to an embodiment. As shown, block 602 determines maximum value range gates and provides the identity of these maximum value range gates in slow-time. In some embodiments, a range FFT is taken over each FMCW chirp, and the maximum valued range gates are determined for each chirp. As time progresses, the maximum value range gates may shift according to the detected heart beat as the relative distance between the millimeter-wave radar sensor and the user moves back and forth due to motion caused by the user's beating heart. Heartbeat signal filter 604, which may be a bandpass filter that performs the filtering steps of step 512 in FIG. 5, provides an extracted heartbeat signal. Smoothing filter 606 further filters the heartbeat signal and heartbeat rate estimation block 608 determines a heartrate from the smoothed heartbeat signal. In some embodiments, smoothing filter 606 is implemented by a Savitzky-Golay filter that essentially performs a k-point regression. Alternatively, other smoothing filters may be used. In some embodiments, block 608 determines the heartrate by measuring the time period of a heartbeat. Alternatively, other methods of determining a frequency of a periodic signal may be used.

Confidence indicator block 610 determines a confidence level of the estimated heart beat using methods described below. In one embodiment, confidence level indicator block 610 provides a confidence level of an estimated heart rate by determining a duration of an amplitude band for an extracted range gate, and determining the percentage of time that the time-window length is within the amplitude band. For example, determining the confidence level may include determining a percentage of time in which the peak-to-average ratio of the determined high response range gates is within a predetermined range. In one example, the amplitude band is taken to be between about 0.8 and 1.2 of a normalized average for a particular range gate or for a group of range gates. If the normalized amplitude of the range gate or the group of range gates is within the amplitude band of 0.8 to 1.2 for 95% of the time window, then a 90% confidence level is assigned to the heartbeat measurement. If the normalized amplitude is within the amplitude band for 75% of the time window, then a 70% confidence level is assigned, and if the normalized amplitude is within the amplitude band for 55% of the time window, then a 50% confidence level is assigned. It should be understood that the numerical values of the normalized amplitude band and the various confidence levels are just one of many possible normalized amplitude band and confidence level definitions that may be used. In alternative embodiments, other values may be assigned. In various embodiments, all of the blocks shown in FIG. 6 may be implemented, for example, using DSP or other processor.

Figure 7A:
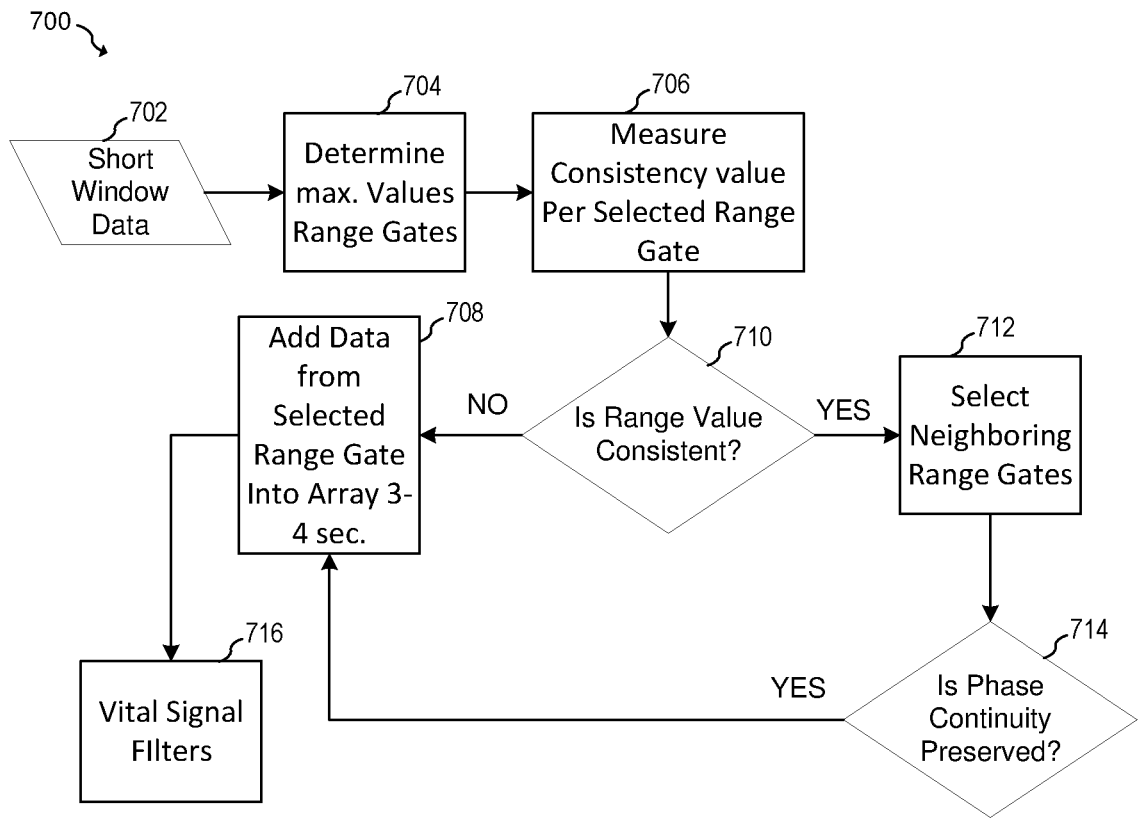
FIGS. 7A and 7B illustrate block diagrams of embodiment confidence level determination algorithms.
Figure 7B:
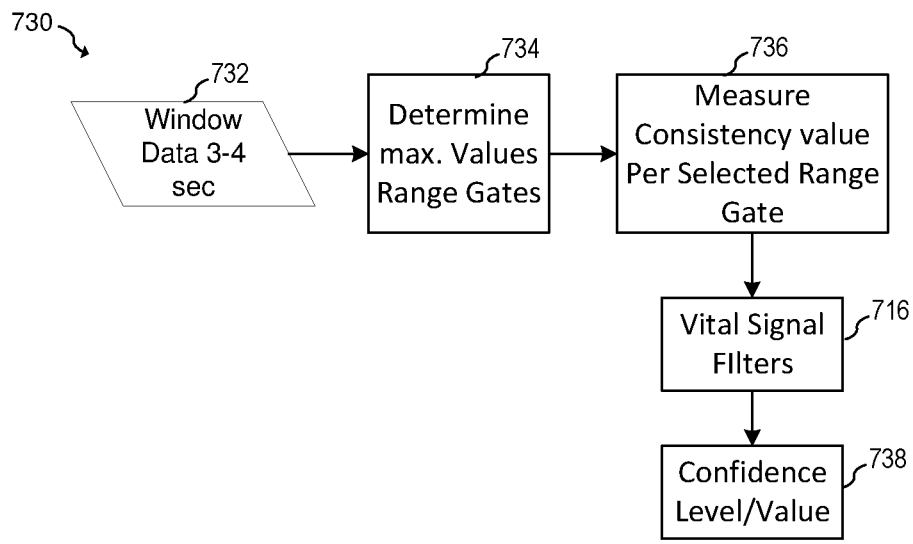

FIGS. 7A and 7B illustrate two example confidence level determination algorithm methods. FIG. 7A illustrates a first embodiment method 700. As shown, in step 704, the maximum range gate values are determined for a set of FMCW data 702 in a short time window. This short time window, which is narrower than the 3-5 second time window described above, may be about 500 µs long in one example. Alternatively, other window time lengths may be used. In step 706, the consistency for each range gate is determined, for example, by determining the percentage of time the amplitude of the particular range gate is within a normalized amplitude band as described above. In step 710, a determination is made as to whether the range gate values are consistent. This determination can be made, for example, by comparing the percentage of time that the amplitude of a particular range gate is within the normalized amplitude to a predetermined threshold. For example, the percentage may be compared with a predetermined threshold of 95%. Alternatively, other percentage threshold may be used.

If step 710 determines that the particular range gate values are consistent, additional data from the 3-5 second time window is appended to the short time window data in step 708 and the next group of short time window data 702 is analyzed. Thus, in various embodiments, a few seconds of data from short time windows may be stitched together to form longer lengths of vital signal data for analysis. In some embodiments, data from the neighboring range gates along with the high response range gates may be stitched together to form a set of modified range gate data. By stitching together data in this fashion, long term motion, as exemplified by shifts in the maximum value range gates, can be compensated for. Thus, in some embodiments, range gate information relevant to vital signal measurements may be segregated from irrelevant range gate information, and the irrelevant range gate information discarded.

If step 710 determines that the particular range gate values are consistent, additional data from the 3-5 second time window is appended to the short time window data in step 708 if phase continuity can be preserved between groups of data as determined in step 714. In various embodiments phase continuity may be preserved, for example, by adding or subtracting a number of samples from the beginning of a second waveform segment and by subtracting or adding a corresponding number of samples from the end of a first waveform segment until phase continuity is achieved. In some embodiments, zeros may be appended to the end the first waveform segment and/or appended to the beginning of the second waveform segment. By preserving phase continuity in this manner, spectral regrowth due to phase discontinuities can be reduced, thereby allowing for more accurate vital signal measurements.

In some embodiments, phase continuity is determined as follows:

$$\hat{P} = \frac{1}{N_w - 1} \sum_{j=1}^{N_w-1} d(\theta_j, \theta_{j+1}),$$

where $\hat{P}$ is the average pairwise phase distance, $\theta_j$ and $\theta_k$ are the relative phases, and $d(\theta_j, \theta_k)$ represents the Euclidean distance (squared distance) or the Manhattan distance (absolute distance). In some embodiments, phase continuity is deemed to exist when P is less than a predetermined phase continuity threshold. In some embodiments, this predetermined phase continuity threshold may be between about 0.01 rad/sec and about 0.5 rad/sec. Alternatively, other thresholds outside of this range may be used depending on the particular embodiment and its specifications. Once data is stitched together from multiple short time windows in step 708, the resulting stitched together data is filtered in step 716 to extract vital signals according to the embodiments described herein.

FIG. 7B illustrates a confidence level determination algorithm method 730 according to a further embodiment in which a confidence level measurement for an entire 3-4 second data window is determined. However, in method 730, the same set of range gates may be used over the course of the entire 3-4 seconds of windowed data 732.

As shown, in step 734, the maximum range gate values are determined for a set of FMCW data 732 in a long time window, for example a 3-4 second time window. Alternatively, other time window lengths can be used. In step 736, the consistency for each range gate is determined, for example, by determining the percentage of time the amplitude of the particular range gate is within a normalized amplitude band as described above. In step 716, range gate data is filtered to extract vital signals according to embodiments described herein, and in step 738, a confidence level/value is generated the corresponds to particular long window data 732 being evaluated using confidence level indication techniques described above.

In various embodiments, method 730 shown in FIG. 7B consumes less power when implemented than method 700 shown in FIG. 7A. In some embodiments, both method 700 shown in FIG. 7A and method 730 shown in FIG. 7B may be performed within the same system. For example, method 730 shown in FIG. 7B may be performed under low power and low power conditions or in situations where there is very little movement between the millimeter-wave radar sensor and the target being measured. In some embodiments, low power conditions may include low battery conditions. In situations where there is very little movement, it is less necessary to stitch together data from different range gates over the course of a long 3-4 second window of data because the same range gates provide vital signal data over longer periods of time. In an alternative embodiment, data from the same range bins may be stitched together over multiple data windows.

In some embodiments, the confidence level produced during step 738 may be used to determine whether to keep using method 730 of FIG. 7B or whether to transition to method 700 of FIG. 7A. For example, if the confidence level is less than a predetermined threshold and/or of the confidence level is less than the predetermined threshold for more than a predetermined number of samples (e.g., over long time window data, short time window data, or a subset thereof), the system may transition to method 700 shown in FIG. 7A in order to increase the detection performance of the system by stitching together data from different range gates.

Figure 8:
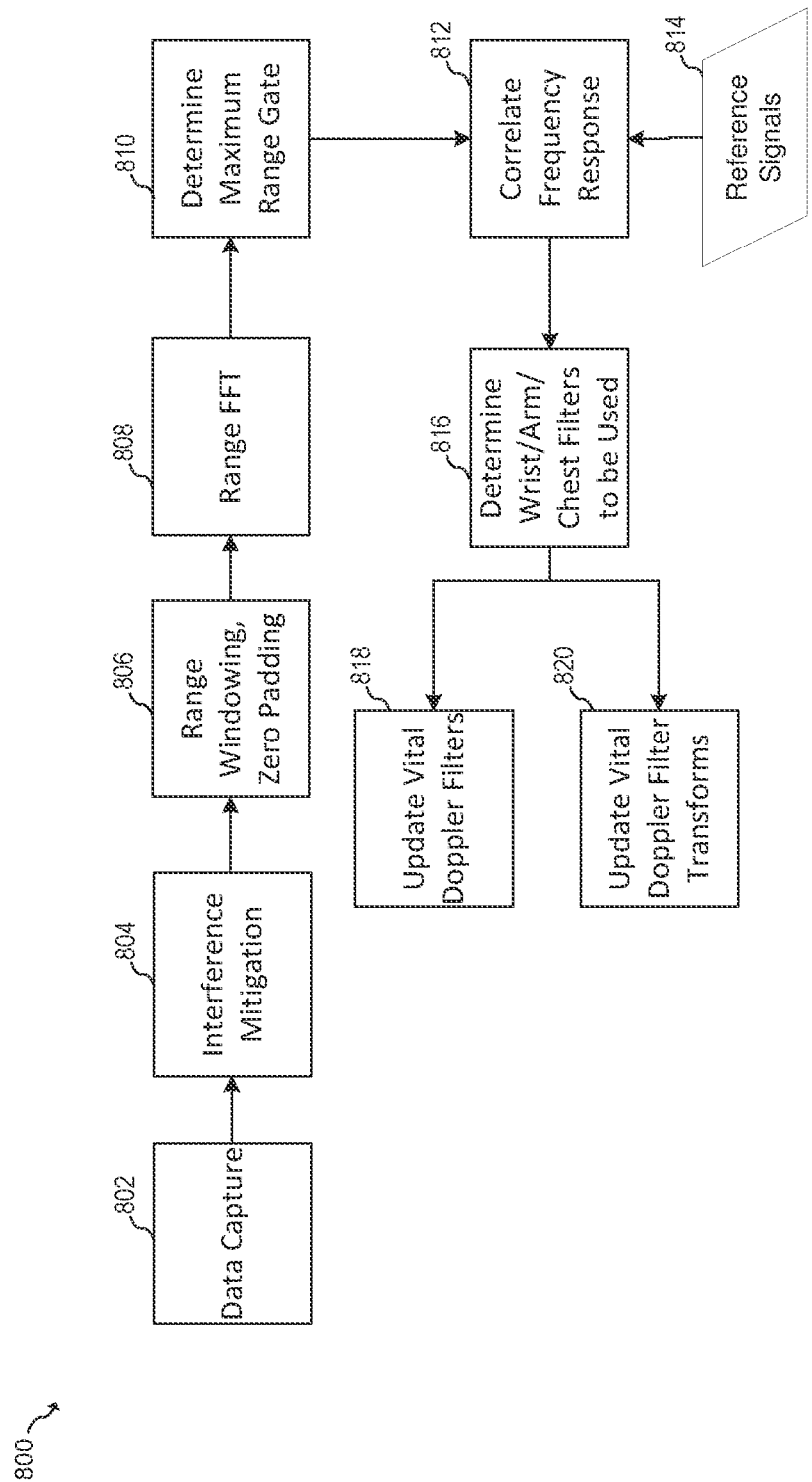
FIG. 8 illustrates a block diagram an embodiment self-calibration data flow method.

FIG. 8 illustrates an embodiment self-calibration data flow method 800 that may be used to optimize vital Doppler filters for a particular physical vital sensor implementation such as a wrist strap, arm strap, chest strap, etc. In step 802, data is captured from the millimeter-wave data sensor. Capturing data may include, for example, receiving digital data from a data bus coupled to the millimeter-wave data sensor. In step 804, interference mitigation is performed. This includes pre-whitening the received radar sensor data for mitigating antenna correlation and colored clutter response. In step 806 range windowing and zero padding is performed in preparation of the range FFT for the sensor data received from each sensor. In this step, a window function is applied to the received radar data followed by zero-padding to improve accuracy along range axis. In step 808, a range FFT is performed on the data received by each sensor and/or each antenna of each sensor on the windowed and zero-padded range data. In step 810, the maximum range gates are determined by evaluating the amplitude of each FFT bin produced by the range FFT of step 808 and determining the maximum FFT bin(s) for each chirp.

In step 812, a frequency response of the determined maximum determined range gates is correlated with reference signals 814. In various embodiments, reference signals 814 are stored reference signals that correspond to a particular use or coupling configuration case such as a wrist-strap, arm strap and/or other coupling scenarios between the radar sensor and the target. In some embodiments, these stored reference signals may include stored reference vital signals such as a reference heartbeat signal. In some embodiments, the reference heartbeat signal is a standard FDA approved heartbeat signal of 60 beats/min.

In an embodiment, slow time data from the selected range bins are correlated with reference signals corresponding to the expected response emanating from an arm, chest or wrist. The response having the highest correlation is selected and the corresponding vital Doppler Filters and the corresponding vital Doppler Filter transform are updated. Different filters and transforms are used due to the different coupling and EM scattering characteristic between the radar sensor and the particular part of the body being monitored. For example, the coupling between the radar sensor and a user's arm is different from the coupling between the radar sensor and a user's chest.

In step 816, filtering functions for the Doppler filters and Doppler transforms are determined based on the correlated frequency response calculated in step 812. Embodiment Doppler filters and Doppler transforms may be implemented using non-linear functions. In some embodiments, method 800 is performed during a factory calibration flow. In various embodiments, the filter setting for the vital Doppler filters and the vital Doppler filter transforms may be used to compensate for signal loss due to the manner in which the physical radar sensor is coupled to the target.

Figure 9:
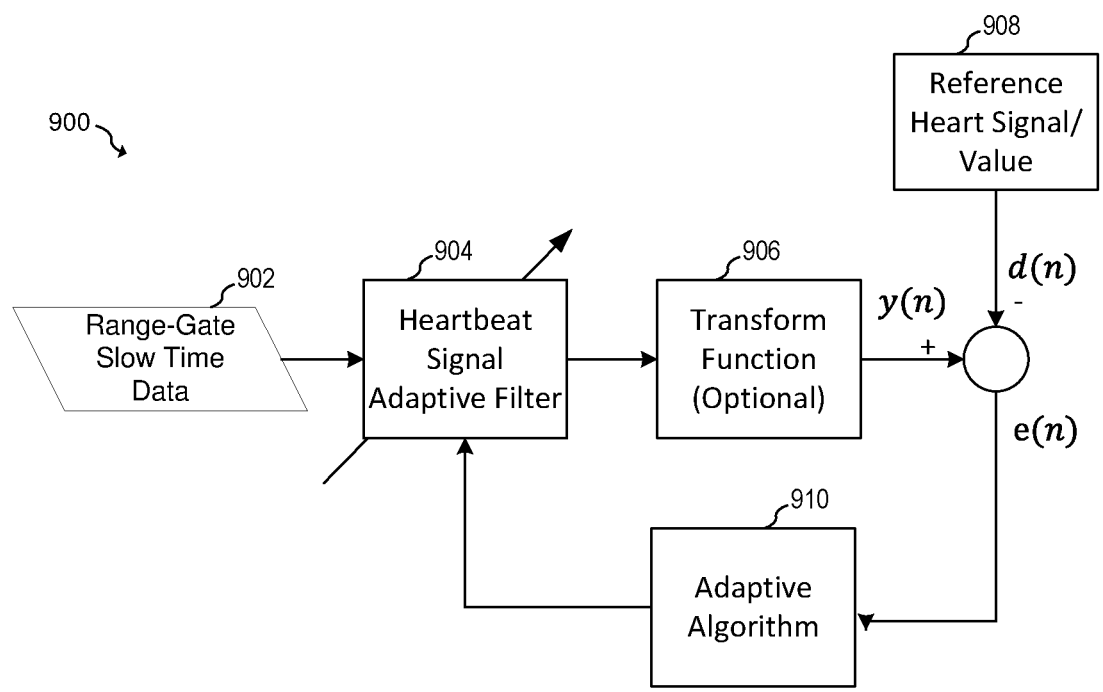
FIG. 9 illustrates an embodiment method of calibrating an embodiment adjustable adaptive filter.

FIG. 9 illustrates an embodiment method 900 of calibrating an embodiment adjustable adaptive filter. In an embodiment, an adaptive algorithm 910 is used to adjust a heartbeat signal adaptive filter 904 such that the error between the output of the heartbeat signal adaptive filter 904 and a reference heart signal/value 908 is minimized or reduced. In other words, the heartbeat signal adaptive filter is calibrated to have a similar signal behavior as reference heart signal value 908 for a particular use case (e.g., wrist strap, arm strap, chest strap, etc.). For example, heartbeat signal adaptive filter may be tuned to produce a measurable heartbeat signal given range gate slow-time data 902 that was generated for the particular use case. Heartbeat signal adaptive filter 904 may also be referred to as correction filter that is configured to correct the range gate data for the manner in which the millimeter-wave radar sensor is coupled to the biological target. Range-gate slow-time data 902 represents captured FMCW data from the system being calibrated for a particular use case. In some embodiments, heartbeat signal adaptive filter 904 is used to compensate for the non-linear transformation undergone by the received radar data due to back scattering. Moreover, in some embodiments, an embodiment calibration procedure may be performed on a human subject.

In some embodiments, reference heart signal/value 908 represents a template heartbeat signal that is based on a normal heartbeat. This template heartbeat signal may be generated by an approved medical organization based on clinically approved measurements. Reference heart signal/value 908 may represent, for example, a normal heartbeat of about 72 beats per minute. Alternatively, other heart rates may be used. In some embodiments, method 900 may be performed during a factory calibration of an embodiment millimeter-wave radar based vital signal sensing system and/or may be performed periodically during used when or if the performance of the millimeter-wave radar based vital signal sensing system degrades over time, or the conditions for comparable results are not obtainable.

In some embodiments, adaptive algorithm 910 may include, for example, a least mean square algorithm, a filter stochastic gradient algorithm, a descent algorithm, or other adaptive algorithm known in the art. For example, a least squares based cost function used by an embodiment least mean square algorithm may be expressed as:

$$J_{LMS}(n) = \Sigma_{i=1}^{N} \alpha(i)(d(i)-y(i))^2,$$

where d(i), y(i) are the reference heart-beat signal and reference signal respectively, α(i) is the pre-defined coefficients that define the LMS cost function. In some embodiments, the heartbeat signal adaptive filter 904 in conjunction with adaptive algorithm may operate according to the following adaptive filter update rule:

$$w_i(n+1) = w_i(n) + \mu(n)g_1(J_{LMS}(n))g_2(n-i)),$$

where $w_i(n)$ refers to the $i^{th}$ coefficient of the adaptive filter at $n^{th}$ iteration of LMS. The above equation is the filter weight update equation, μ(n) is the step-size which can be independent of the iteration as well, $g_1(.)$ and $g_2(.)$ are some functions based on LMS type. For instance batc-LMS, $g_1(.)$ is a derivative w.r.t. y(i), and $g_2(.)$ is the identity function. For sign-RMS, $g_2(.)$ is the sign function, etc.

In some embodiments, an optional transform function 906 may be used to reduce adaptive filter convergence or reduce computational complexity. The transform function may be expressed as:

$$y(n) = f(W(n), y(n-1), \ldots y(1)),$$

where f (.) defines the transformation which is a function of the input data {y(n−1), . . . y(1)} and the kernel W(n). In various embodiment, transform function 906 may be used to maximize FFT operation when the filter is being fit to an absolute heart-beat while disregarding the subtleties of other frequency components in the heart signal. In some embodiments, a DCT transformation could be used to represent the heartbeat signal using a lower number of coefficients, thereby reducing the computational complexity of the filter and reducing its convergence time.

Figure 10A:
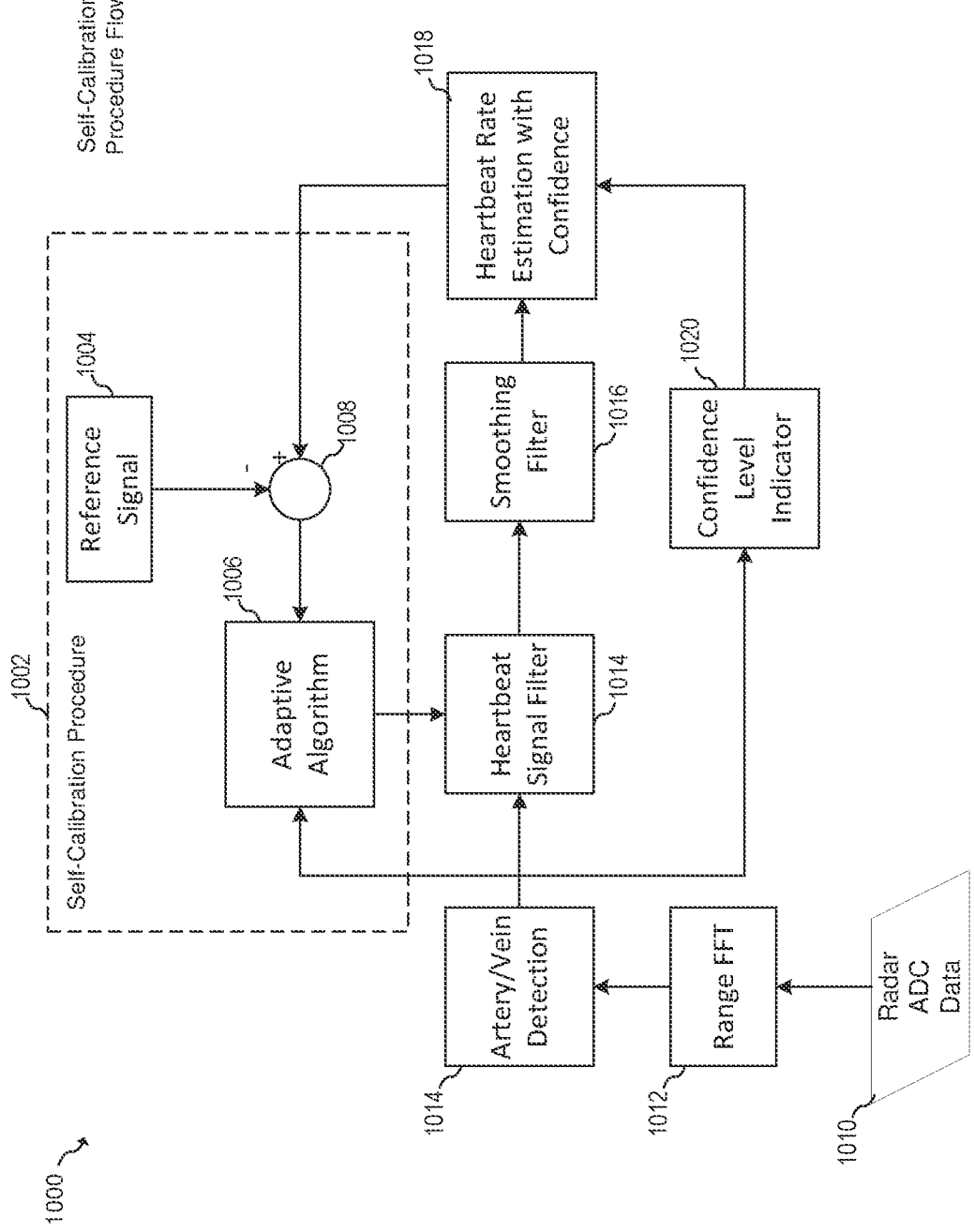
FIG. 10A illustrates a block diagram of an embodiment self-calibration procedure flow.
Figure 10B:
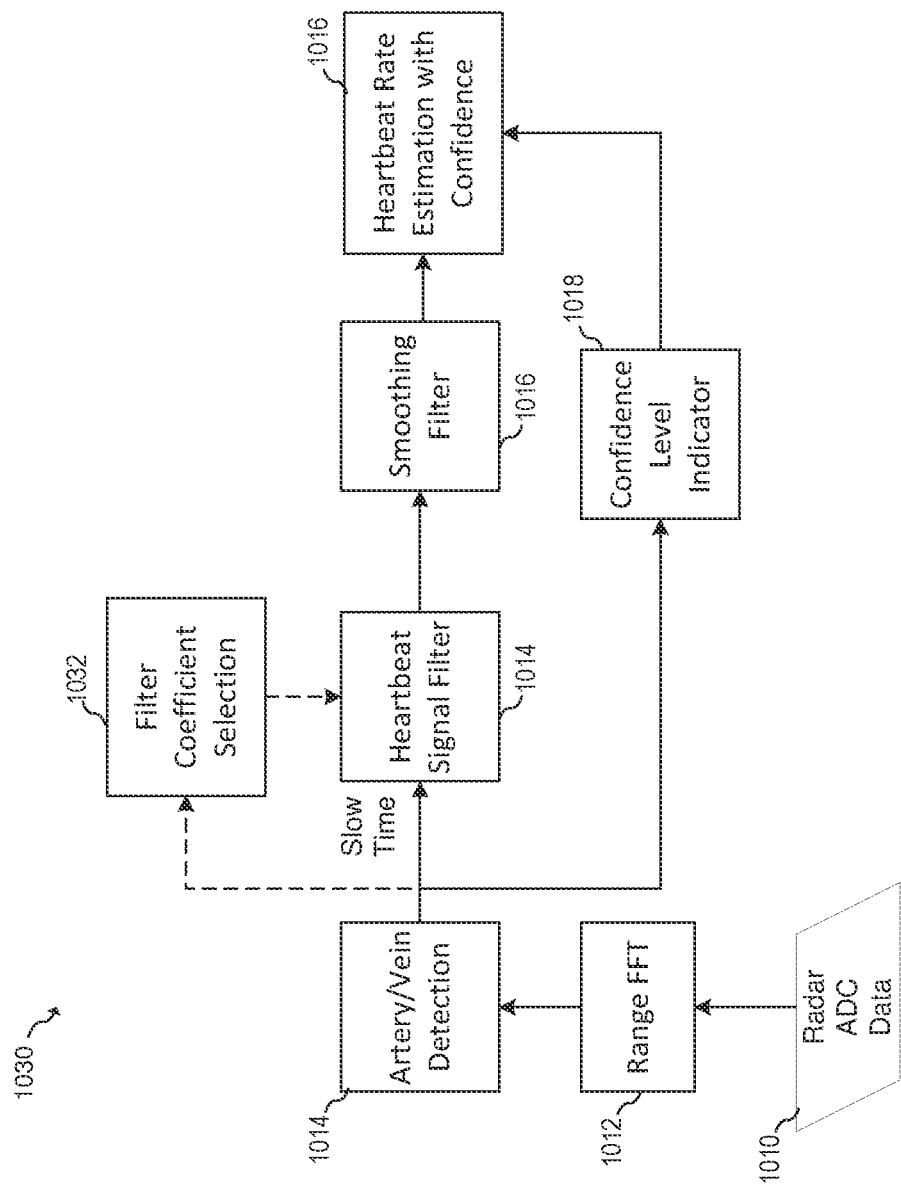
FIG. 10B illustrates a corresponding embodiment run-time procedure flow.

FIG. 10A illustrates a self-calibration procedure flow 1000 and FIG. 10B illustrates a corresponding run-time procedure flow 1030 according to an embodiment of the present invention. The procedure flows of FIGS. 10A and 10B may be used in any embodiment millimeter-wave based vital signal sensing system.

During self-calibration procedure flow 1010 shown in Figure RA, a range FFT 1012 is performed on radar analog-to-digital converter (ADC) data 1010 that was captured using an embodiment millimeter-wave radar sensor, such as those described above. Artery/vein detection algorithm, which is described with respect to FIG. 11 below, determines a heartbeat signal, which is filtered by heartbeat signal filter 1014. Heartbeat signal filter 1014 may be implemented, for example, using a bandpass filter to extract a filtered heartbeat signal. Smoothing filter 1016 smooths the output of the heartbeat signal filter 1014 and heartbeat estimation block 1016 determines a heartrate from the smoothed heartbeat signal. Smoothing filter 1016 may be implemented, for example using a $15^{th}$ order Savitzky-Golay filter, which essentially implements a 15 point regression. Alternatively, other filter types can be used.

In some embodiments, heartbeat estimation block 1016 determines the heartrate by measuring the time period of a heartbeat. Alternatively, other methods of determining a frequency of a periodic signal may be used. Confidence level indicator 1020 determines a confidence level of the estimated heart beat using confidence level determination methods described above. In some embodiments, the determined confidence level may be used to select the algorithm used by heartbeat rate estimation block 1018. For example, when confidence level indicator 1020 indicates a high confidence a high confidence level, a lower complexity algorithm could be used by heartbeat rate estimation block 1018 in order to save power.

During self-calibration procedure 1002, error determination block 1008 produces an error signal by determining a difference between reference signal 1004 and the estimated heartrate determined by heartbeat estimation block 1016. In some embodiments, error determination block 1008 may be implemented by subtracting reference signal 1004 from the output of heartbeat rate estimation block 1018. In various embodiments, adaptive algorithm 1006 updates the filter coefficients of heartbeat signal filter 1014 in order to reduce the error signal determined by error determination block 1008. The operation of adaptive algorithm 1006 in conjunction with reference signal 1004 and heartbeat signal filter 1014 may proceed in a similar manner as the calibration method described above with respect to FIG. 9. In some embodiments, a plurality of sets of coefficients directed toward various use cases may be derived using self-calibration procedure 1002. For example, a first set of filter coefficients for heartbeat signal 1014 may be derived for a wrist strap, a second set of filter coefficients may derived for an arm strap, a third set of filter coefficients may be derived for a chest strap and so on.

During self-calibration, the user may attach the millimeter-wave radar sensor to his or her body in the applicable manner (e.g., wrist strap, arm strap, chest strap, etc.) and initiate the self-calibration procedure. Thus, each set of radar ADC data 1010 taken during the self-calibration procedure represents FMCW data derived for a particular use case. Once one or more self-calibration procedures are complete, the various sets of filter coefficients for heartbeat signal filter 1014 may be stored in memory for later retrieval during operation.

FIG. 10B illustrates the corresponding run-time procedure flow 1030 that represents the procedure flow that an embodiment vital signal detection system may use during normal operation. Range FFT 1012, artery/vein detection 1014, heartbeat signal filter 1014, smoothing filter 1016, heartbeat rate estimation block 1018 and confidence level indicator 1020 operate as described above with respect to FIG. 10A. During operation, however, filter coefficient selection block 1032 adaptively detects the use case best represented by radar ADC data 1010. For example, filter coefficient selection block 1032 may determine whether the user is using a wrist strap, arm strap, or chest strap, and loads the corresponding coefficients that were derived during the self-calibration procedure flow 1010 shown in FIG. 10A. In one example, filter coefficient selection block 1032 may include the functionality of blocks 812, 816, 818 and 820 shown in FIG. 8.

In various embodiments, filter coefficient selection block determines the set of coefficients based on signal path characteristics of the monitoring scenario and the particular portions of the body being monitored. An initial set of coefficients are first selected during self-calibration as described above with respect to FIG. 10A. These coefficients may be adaptively updated as described hereinabove with respect to FIG. 9. Once the coefficients for different use cases are derived, a particular use case is identified for operation as described above with respect to block 816 of FIG. 8, and the coefficients corresponding to the selected use case are selected as filter coefficients. For example, if filter coefficient selection block 1032 determines that radar ADC data 1010 is obtained in a system in which the millimeter-wave radar sensor is coupled to the user's wrist via a wrist strap or a wrist watch, then the applicable coefficients are loaded into heartbeat signal filter 1014. On the other hand, if filter coefficient selection block 1032 determines that radar ADC data 1010 is obtained in a system in which the millimeter-wave radar sensor is coupled to the user's chest via a chest strap, then the coefficients applicable to the chest strap are loaded into heartbeat signal filter 1014.

Figure 11:
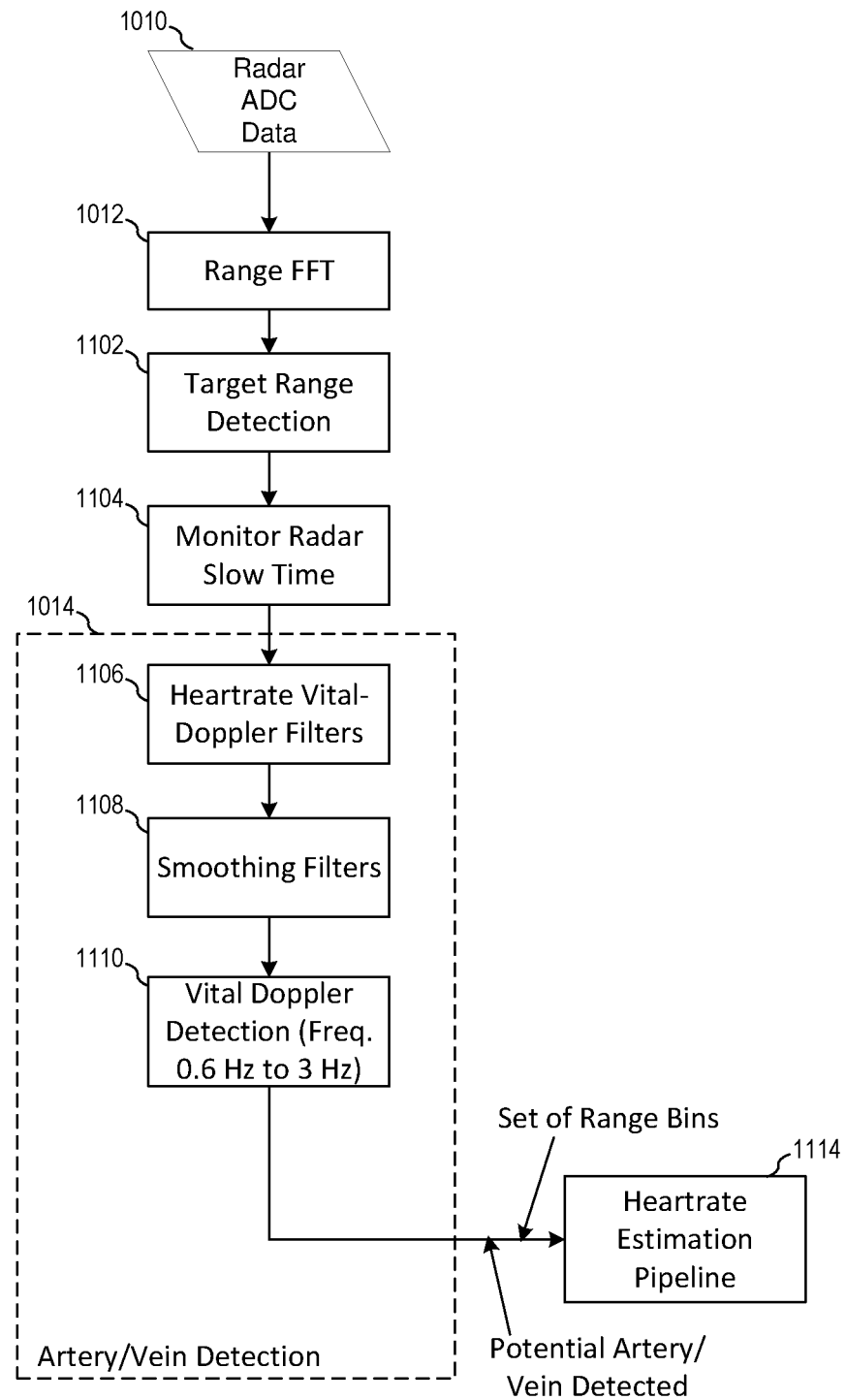
FIG. 11 illustrates a block diagram of an embodiment artery/vein detection method.

FIG. 11 illustrates a block diagram of an embodiment artery/vein detection method 1014 situated in the context of other processing steps that occur prior to and after the artery/vein detection method 1014. As shown, range FFT block 1012 performs a range FFT of radar ADC data 1010. A target range detection is performed on the range FFT and the output of target range detection block 1102 is monitored by monitor radar slow-time block 1104. In some embodiments, target range selection block 1102 extracts the range gates with the highest response, and monitor radar slow-time block 1104 monitors the extracted range gates by storing the slow-time radar data along the detected range bins.

Artery/vein detection block 1014 determines whether the extracted range gates represent an artery or a vein by applying heartrate vital-Doppler filters 1106 to the values of the extracted range gates. In some embodiments, vital-Doppler filters 1106 include low bandwidth filtering at 0.6 Hz-3 Hz. The output of heartrate micro-Doppler filters 1106 is smoothed using smoothing filters 1108, and vital Doppler detection block 1110 filters the output of smoothing filters 1108 in order to detect whether or not a heartbeat signal is present. In some embodiments, vital Doppler detection block 1110 is implemented as a threshold detector to discriminate between valid vital signal and noise.

Vital Doppler detection block 1110 compares the output of smoothing filters 1108 with a predetermined threshold. In some embodiments, the predetermined threshold may be about 3 dB above the noise floor. However, in alternative embodiments, other threshold values may be used. If the output of vital Doppler detection block 1110 exceeds the predetermined threshold, a potential artery/vein is considered to be detected, and the set of detected range bins are process by heartrate estimation pipeline 1114.

Figure 12:
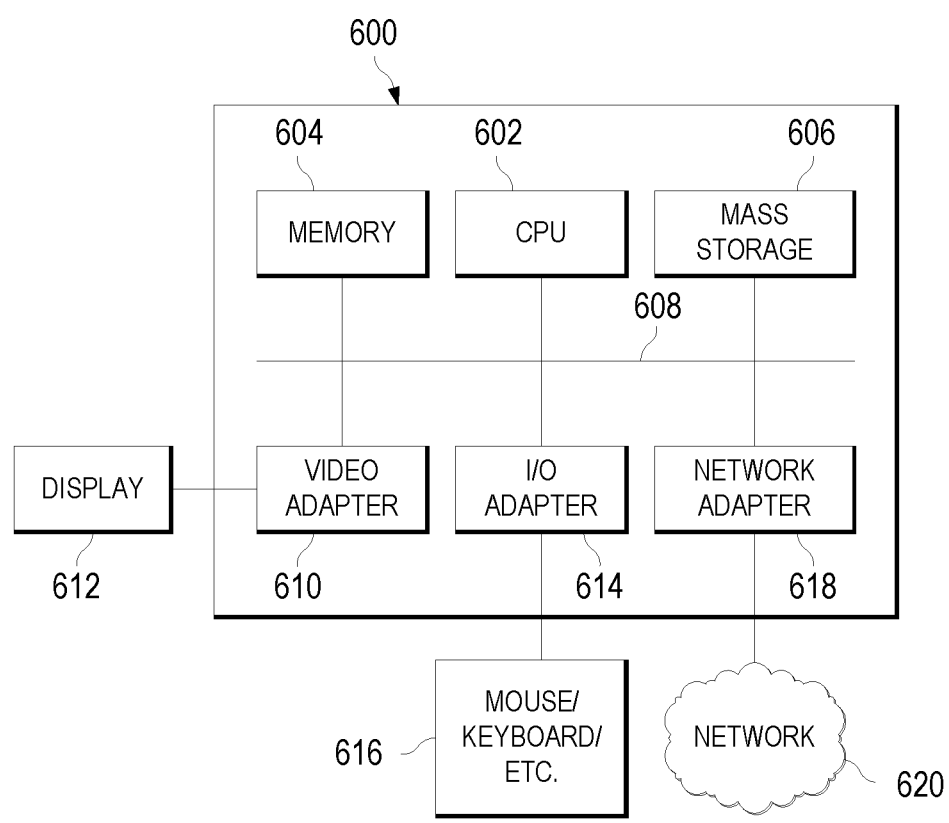
FIG. 12 illustrates a block diagram of a processing system that may be used to implement portions of embodiment vital signal detection systems.

Referring now to FIG. 12, a block diagram of a processing system 1200 is provided in accordance with an embodiment of the present invention. The processing system 1200 depicts a general-purpose platform and the general components and functionality that may be used to implement portions of the embodiment vital signal sensing system and/or an external computer or processing device interfaced to the embodiment vital signal sending system. The processing system 1200 may include, for example, a central processing unit (CPU) 1202, memory 1204, and a mass storage device 1206 connected to a bus 1208 configured to perform the processes discussed above. The processing system 1200 may further include, if desired or needed, a video adapter 1210 to provide connectivity to a local display 1212 and an input-output (I/O) Adapter 1214 to provide an input/output interface for one or more input/output devices 616, such as a mouse, a keyboard, printer, tape drive, CD drive, or the like.

The processing system 1200 also includes a network interface 1218, which may be implemented using a network adaptor configured to be coupled to a wired link, such as an Ethernet cable, USB interface, or the like, and/or a wireless/cellular link for communications with a network 1220. The network interface 1218 may also comprise a suitable receiver and transmitter for wireless communications. It should be noted that the processing system 1200 may include other components. For example, the processing system 1200 may include power supplies, cables, a motherboard, removable storage media, cases, and the like. These other components, although not shown, are considered part of the processing system 1200.

Example embodiments of the present invention are summarized here. Other embodiments can also be understood from the entirety of the specification and the claims filed herein.

Example 1. A device for measuring vital signals includes a first circuit board layer comprising a first insulator material; a first integrated circuit disposed on the first circuit board layer, the first integrated circuit including a millimeter-wave radar sensor and a digital interface configured to provide digitized baseband radar signals; a second integrated circuit coupled to the first integrated circuit and disposed on the first circuit board layer, the second integrated circuit including a digital signal processor (DSP) configured to determine vital signal information based on the digitized baseband radar signals; a second circuit board layer including a second insulator material, the second circuit board layer having a first surface disposed over a first surface of the first circuit board layer; a transmit antenna disposed on the second circuit board layer and coupled to the first integrated circuit; and a receive antenna disposed on the second circuit board layer and coupled to the first integrated circuit.

Example 2. The device of example 1, where the first insulator material is the same as the second insulator material.

Example 3. The device of example 1 or 2, further including a third integrated circuit disposed on the first circuit board layer and coupled to the second integrated circuit, wherein the third integrated circuit includes a memory.

Example 4. The device of one of examples 1-3, where the first integrated circuit is disposed on a second surface of the first circuit board layer opposite the first surface.

Example 5. The device of claim 4, where the second integrated circuit is disposed on the second surface of the first circuit board layer opposite the first surface of the first circuit board layer.

Example 6. The device of example 4, where the second integrated circuit is disposed within the first surface of the first circuit board layer.

Example 7. The device of one of examples 4-6, where the transmit antenna and the receive antenna include a conductive material disposed on a second surface of the second circuit board layer opposite the first surface of the second circuit board layer; the transmit antenna is coupled to the first integrated circuit via a first via that extends through the first circuit board layer and the second circuit board layer; and the receive antenna is coupled to the first integrated circuit via a first via that extends through the first circuit board layer and the second circuit board layer.

Example 8. The device of one of examples 4-7, further including a ground plane having a conductive layer disposed between the first circuit board layer and the second circuit board layer.

Example 9. The device of one of examples 4-7, further including a third circuit board layer disposed between the first circuit board layer and the second circuit board layer.

Example 10. The device of one of examples 1 or 2, where the first integrated circuit is stacked on top of the second integrated circuit; the first integrated circuit is embedded within the first surface of the first circuit board layer; and the second integrated circuit is embedded within a second surface of the first circuit board layer opposite the first surface of the first circuit board layer.

Example 11. The device of claim 10, further including a third integrated circuit disposed next to the second integrated circuit, wherein the first integrated circuit is further stacked on top of the third integrated circuit, a first portion of a first surface of the first integrated circuit is adjacent to a first surface of the second integrated circuit, a second portion of the first surface of the first integrated circuit is adjacent to a first surface of the third integrated circuit, and the third integrated circuit comprises a memory.

Example 12. The device of one of examples 10 and 11, where the transmit antenna and the receive antenna include a conductive material disposed on a second surface of the second circuit board layer opposite the first surface of the second circuit board layer; the transmit antenna is coupled to the first integrated circuit via a first via that extends through the second circuit board layer; and the receive antenna is coupled to the first integrated circuit via a second via that extends through the second circuit board layer.

Example 13. A device for measuring vital signals including a redistribution layer comprising an insulating material; a first integrated circuit having a first surface disposed on a first side of the redistribution layer, the first integrated circuit including a millimeter-wave radar sensor and a digital interface configured to provide digitized baseband radar signals; a second integrated circuit having a first surface disposed on the first side of the redistribution layer and coupled to the first integrated circuit, the second integrated circuit including a digital signal processor DSP configured to determine vital signal information based on the digitized baseband radar signals; a transmit antenna disposed in the redistribution layer and coupled to the first integrated circuit via a first conductive layer of the redistribution layer; a receive antenna disposed in the redistribution layer coupled to the first integrated circuit via a first conductive layer of the redistribution layer; and a molding material disposed over a second side of the first integrated circuit, a second side of the second integrated circuit and the first side of the redistribution layer.

Example 14. The device of example 13, where the transmit antenna and the receive antenna are implemented in the first conductive layer; and the first conductive layer is disposed at the first surface of the redistribution layer.

Example 15. The device of one of examples 13 or 14, where the redistribution layer, first integrated circuit, second integrated circuit, transmit antenna, receive antenna and molding material form an embedded wafer level ball grid array (eWLB) package.

Example 16. The device of example 15, where the transmit antenna and the receive antenna are disposed in a fan out area of the eWLB package.

Example 17. A system including a wearable object configured to be worn by a person; and a millimeter-wave radar system mounted on the wearable object, the millimeter-wave radar system including a circuit board, millimeter-wave radar sensor disposed on the circuit board, a plurality of antennas coupled to the millimeter-wave radar sensor and disposed on the circuit board adjacent to the millimeter-wave radar sensor, and a processing circuit coupled to the millimeter-wave radar sensor and disposed on the circuit board, where the processing circuit is configured to determine vital signal information of the person based on output from the millimeter-wave radar sensor.

Example 18. The system of example 17, where the wearable object includes a wrist band.

Example 19. The system of example 17, where the wearable object includes a chest strap.

Example 20. The system of one of examples 17-19, where the vital signal information includes a heart rate.

Example 21. The system of one of examples 17-20, where the processing circuit is further configured to instruct the millimeter-wave radar sensor to perform a first set of radar measurements to produce a first set of radar data; determine a first set of range gate measurements from the first set of radar data; determine high response range gates from the first set of range gate measurements; apply a correction filter to the determined high response range gates in slow-time to produce corrected range gate data, the correction filter configured to correct for a manner in which the millimeter-wave radar sensor is coupled to the person via the wearable object; and apply a vital signal filter to the corrected range gate data to determine the vital signal information of the person.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A system comprising:
a wearable object configured to be worn by a person; and
a millimeter-wave radar system mounted on the wearable object, the millimeter-wave radar system comprising:
a circuit board,
a millimeter-wave frequency modulated continuous wave (FMCW) radar sensor disposed on the circuit board, the millimeter-wave FMCW radar sensor configured to generate beat frequencies proportional to a distance between the millimeter-wave radar system and a sensed object,
a plurality of antennas coupled to the millimeter-wave FMCW radar sensor and disposed on the circuit board adjacent to the millimeter-wave FMCW radar sensor, and
a processing circuit coupled to the millimeter-wave FMCW radar sensor and disposed on the circuit board, wherein the processing circuit is configured to:
instruct the millimeter-wave FMCW radar sensor to perform a first set of radar measurements to produce a first set of radar data based on the beat frequencies from the millimeter-wave FMCW radar sensor,
determine a first set of range gate measurements from the first set of radar data,
determine high response range gates from the first set of range gate measurements,
apply a correction filter to the determined high response range gates in slow-time to produce corrected range gate data, the correction filter configured to correct for a coupling between the millimeter-wave FMCW radar sensor and the person, and
apply a vital signal filter to the corrected range gate data to determine vital signal information of the person.

2. The system of claim 1, wherein the wearable object comprises a wrist band.

3. The system of claim 1, wherein the wearable object comprises a chest strap.

4. The system of claim 1, wherein the vital signal information comprises a heart rate.

5. The system of claim 1, wherein:
the millimeter-wave FMCW radar sensor is disposed on a first integrated circuit; and
the processing circuit is disposed on a second integrated circuit.

6. The system of claim 1, wherein:
the circuit board comprises a first circuit board layer comprising a first insulator material, and a second circuit board layer comprising a second insulator material disposed over a first surface of the first circuit board layer; and
the millimeter-wave FMCW radar sensor and the processing circuit are disposed on the first circuit board layer.

7. The system of claim 6, wherein the plurality of antennas comprises:
a transmit antenna disposed on the second circuit board layer; and
a receive antenna disposed on the second circuit board layer.

8. The system of claim 6, wherein further comprising a ground plane disposed between the first circuit board layer and the second circuit board layer.

9. A system comprising:
a millimeter-wave radar system configured to be mounted on a wearable object, the millimeter-wave radar system comprising:
a circuit board,
a millimeter-wave frequency modulated continuous wave (FMCW) radar sensor disposed on the circuit board, the millimeter-wave FMCW radar sensor configured to generate beat frequencies proportional to a distance between the millimeter-wave radar system and a sensed object,
a plurality of antennas coupled to the millimeter-wave FMCW radar sensor and disposed on the circuit board adjacent to the millimeter-wave FMCW radar sensor, and
a processing circuit coupled to the millimeter-wave FMCW radar sensor and disposed on the circuit board, the processing circuit is configured to:
instruct the millimeter-wave FMCW radar sensor to perform a first set of radar measurements to produce a first set of radar data based on the beat frequencies from the millimeter-wave FMCW radar sensor,
determine a first set of range gate measurements from the first set of radar data;
determine high response range gates from the first set of range gate measurements,
apply a correction filter to the determined high response range gates in slow-time to produce corrected range gate data, the correction filter configured to correct for a coupling between the millimeter-wave FMCW radar sensor and a person wearing the wearable object, and
apply a vital signal filter to the corrected range gate data to determine vital signal information of the person wearing the wearable object.

10. The system of claim 9, wherein:
the circuit board comprises a ground plane;
the millimeter-wave FMCW radar sensor and the processing circuit are disposed on a first side of the ground plane; and
the plurality of antennas are disposed on a second side of the ground plane opposite the first side.

11. The system of claim 10, wherein:
the millimeter-wave FMCW radar sensor and the processing circuit are disposed on a first insulating layer on the first side of the ground plane; and
the plurality of antennas are disposed on a second insulating layer on the second side of the ground plane opposite the first side.

12. The system of claim 11, wherein the second insulating layer comprises a plurality of second insulating layers.

13. The system of claim 10, wherein:
the millimeter-wave FMCW radar sensor and the processing circuit are disposed within a first insulating layer on the first side of the ground plane; and
the plurality of antennas are disposed on a second insulating layer on the second side of the ground plane opposite the first side.

14. The system of claim 13, wherein the millimeter-wave FMCW radar sensor and the processing circuit are stacked on top of each other.

15. The system of claim 10, wherein:
the millimeter-wave FMCW radar sensor is disposed on disposed on a first insulating layer on the first side of the ground plane;
the processing circuit is disposed in the first insulating layer on the first side of the ground plane; and the plurality of antennas are disposed on a second insulating layer on the second side of the ground plane opposite the first side.

16. The system of claim 9, wherein:
the circuit board comprises a redistribution layer;
the millimeter-wave FMCW radar sensor and the processing circuit are disposed on a first side of the redistribution layer; and
the plurality of antennas comprise conductive regions disposed in the redistribution layer.

17. A method of operating a millimeter-wave radar system configured to be mounted on a wearable object, the millimeter-wave radar system comprising a circuit board, a millimeter-wave frequency modulated continuous wave (FMCW) radar sensor disposed on the circuit board, a plurality of antennas coupled to the millimeter-wave FMCW radar sensor and disposed on the circuit board adjacent to the millimeter-wave FMCW radar sensor, and a processing circuit coupled to the millimeter-wave FMCW radar sensor and disposed on the circuit board, the method comprising:
generating, by the FMCW radar sensor, beat frequencies proportional to a distance between the millimeter-wave radar system and a sensed object;
instructing the millimeter-wave FMCW radar sensor to perform a first set of radar measurements to produce a first set of radar data based on the beat frequencies from the millimeter-wave FMCW radar sensor;
determining a first set of range gate measurements from the first set of radar data;
determining high response range gates from the first set of range gate measurements;
applying a correction filter to the determined high response range gates in slow-time to produce corrected range gate data, the correction filter configured to correct for a coupling between the millimeter-wave FMCW radar sensor and a person wearing the wearable object; and
applying a vital signal filter to the corrected range gate data to determine vital signal information of the person wearing the wearable object.

18. The method of claim 17, wherein the wearable object comprises a wrist band.

19. The method of claim 17, wherein the wearable object comprises a chest strap.

20. The method of claim 17,, wherein the vital signal information comprises a heart rate.

\* \* \* \* \*